(12) United States Patent
Fruchey et al.

(10) Patent No.: US 8,193,375 B2
(45) Date of Patent: Jun. 5, 2012

(54) PROCESSES FOR THE PRODUCTION OF HYDROGENATED PRODUCTS

(75) Inventors: Olan S. Fruchey, Hurricane, WV (US); Leo E. Manzer, Wilmington, DE (US); Dilum Dunuwila, Princeton, NJ (US); Brian Terry Keen, Pinch, WV (US); Brooke Ashley Albin, Charleston, WV (US); Nye A. Clinton, Hurricane, WV (US); Bernard Duane Dombek, Charleston, WV (US)

(73) Assignee: BioAmber International S.à.r.l., Luxembourg (LU)

( * ) Notice: Subject to any disclaimer, the term of this patent is extended or adjusted under 35 U.S.C. 154(b) by 0 days.

(21) Appl. No.: 13/213,565

(22) Filed: Aug. 19, 2011

(65) Prior Publication Data

US 2011/0301364 A1    Dec. 8, 2011

Related U.S. Application Data

(63) Continuation of application No. 13/051,688, filed on Mar. 18, 2011.

(60) Provisional application No. 61/320,074, filed on Apr. 1, 2010.

(51) Int. Cl.
*C07D 307/00* (2006.01)
*C07D 305/00* (2006.01)
*C07C 27/04* (2006.01)

(52) U.S. Cl. .......................... 549/326; 549/508; 568/864

(58) Field of Classification Search .................. 549/326, 549/508; 568/864
See application file for complete search history.

(56) References Cited

U.S. PATENT DOCUMENTS

| | | | |
|---|---|---|---|
| 4,782,167 A | 11/1988 | Rao | |
| 5,034,105 A | 7/1991 | Berglund et al. | |
| 5,143,833 A | 9/1992 | Datta | |
| 5,958,744 A | 9/1999 | Berglund et al. | |
| 6,265,190 B1 | 7/2001 | Yedur et al. | |
| 7,186,856 B2 | 3/2007 | Meng et al. | |
| 7,199,250 B2 | 4/2007 | Werpy et al. | |
| 7,217,837 B2 | 5/2007 | Isotani | |
| 2005/0070738 A1 | 3/2005 | Isotani | |
| 2007/0161816 A1 | 7/2007 | Isotani | |
| 2009/0137843 A1 | 5/2009 | Isotani | |
| 2010/0044626 A1 | 2/2010 | Fischer et al. | |
| 2010/0094051 A1 | 4/2010 | Nishi et al. | |
| 2010/0145072 A1 | 6/2010 | Werpy et al. | |

FOREIGN PATENT DOCUMENTS

| | | |
|---|---|---|
| JP | 2005-132836 A | 5/2005 |
| JP | 2005-139156 | 6/2005 |
| JP | 2007-254354 A | 10/2007 |
| JP | 2008-056624 A | 3/2008 |
| WO | 2010/003728 A1 | 1/2010 |

OTHER PUBLICATIONS

Datsenko, K.A. et el, "One-Step Inactivation of Chromosomal Genes in *Escherichia coli* K-12 Using PCR Products", *Proc. Natl. Acad Sci.* Jun. 6, 2000, vol. 97, No. 12, pp. 6640-6645.
Bochner, B.R. et al., "Positive Selection for Loss of Tetracycline Resistance," *Journal of Bacteriology*, Aug. 1980, vol. 143, No. 2, pp. 926-933.
Sundaramurthi, P. et al., "Calorimetric and Diffractometric Evidence for the Sequential Crystallization of Buffer Components and the Consequential pH Swing in Frozen Solutions," *J. Phys. Chem. B*, 2010, vol. 114, pp. 4915-4923.
Sundaramurth, P. et al., "'pH Swing' in Frozen Solutions—Consequence of Sequential Crystallization of Buffer Components," *The Journal of Physical Chemistry Letters*, 2010, vol. 1, pp. 265-268.
Vanderzee, C.E. et al., "Enthalpies of Formation of Mono- and Diammonium Saccinates and of Aqueous Ammonia and Ammonia and Ammonium Ion," *J. Chem. Thermodynamics*, 1972, vol. 4, pp. 541-550.

*Primary Examiner* — Nizal Chandrakumar
(74) *Attorney, Agent, or Firm* — DLA Piper LLP (US)

(57) ABSTRACT

A process for making a hydrogenated product includes providing a clarified DAS-containing fermentation broth, distilling the broth to form an overhead that includes water and ammonia, and a liquid bottoms that includes MAS, at least some DAS, and at least about 20 wt % water, cooling and/or evaporating the bottoms, and optionally adding an antisolvent to the bottoms, to attain a temperature and composition sufficient to cause the bottoms to separate into a DAS-containing liquid portion and a MAS-containing solid portion that is substantially free of DAS, separating the solid portion from the liquid portion, recovering the solid portion, hydrogenating the second solid portion in the presence of at least one hydrogenation catalyst to produce the hydrogenated product comprising at least one of THF, GBL or BDO, and recovering the hydrogenated product.

10 Claims, 9 Drawing Sheets

PROCESSES FOR THE PRODUCTION OF HYDROGENATED PRODUCTS

RELATED APPLICATIONS

This application is a continuation of US application Ser. No. 13/051,688, which claims the benefit of U.S. Provisional Application No. 61/320,074, filed Apr. 1, 2010, the subject matter of which is hereby incorporated by reference.

TECHNICAL FIELD

This disclosure relates to processes for producing hydrogenated products, particularly 1,4-butanediol (BDO), tetrahydrofuran (THF), and gamma-butyrolactone (GBL) from succinic acid (SA) produced by fermentation.

BACKGROUND

Certain carbonaceous products of sugar fermentation are seen as replacements for petroleum-derived materials for use as feedstocks for the manufacture of carbon-containing chemicals. One such product is MAS.

A material related to MAS, namely SA, can be produced by microorganisms using fermentable carbon sources such as sugars as starting materials. However, most commercially viable, succinate producing microorganisms described in the literature neutralize the fermentation broth to maintain an appropriate pH for maximum growth, conversion and productivity. Typically, the pH of the fermentation broth is maintained at or near a pH of 7 by introduction of ammonium hydroxide into the broth, thereby converting the SA to DAS.

Kushiki (Japanese Published Patent Application, Publication No. 2005-139156) discloses a method of obtaining MAS from an aqueous solution of DAS that could be obtained from a fermentation broth to which an ammonium salt is added as a counter ion. Specifically, MAS is crystallized from an aqueous solution of DAS by adding acetic acid to the solution to adjust the pH of the solution to a value between 4.6 and 6.3, causing impure MAS to crystallize from the solution.

Masuda (Japanese Unexamined Application Publication P2007-254354, Oct. 4, 2007) describes partial deammoniation of dilute aqueous solutions of "ammonium succinate" of the formula $H_4NOOCCH_2CH_2COONH_4$. From the molecular formula disclosed, it can be seen that "ammonium succinate" is diammonium succinate. Masuda removes water and ammonia by heating solutions of the ammonium succinate to yield a solid SA-based composition containing, in addition to ammonium succinate, at least one of MAS, SA, monoamide succinate, succinimide, succinamide or ester succinate. Thus, it can be inferred that like Kushiki, Masuda discloses a process that results in production of impure MAS. The processes of both Kushiki and Masuda lead to materials that need to be subjected to various purification regimes to produce high purity MAS.

Bio-derived SA such as that derived from MAS is a platform molecule for synthesis of a number of commercially important chemicals and polymers. Therefore, it is highly desirable to provide a purification technology that offers flexibility to integrate clear, commercially viable paths to derivatives such as BDO, THF and GBL. In response to the lack of an economically and technically viable process solution for converting fermentation-derived SA to BDO, THF, and GBL, it could be helpful to provide methods for providing a cost effective SA stream of sufficient purity for direct hydrogenation.

SUMMARY

We provide a process for making a hydrogenated product including providing a clarified DAS-containing fermentation broth, distilling the broth to form a first overhead that comprises water and ammonia, and a first liquid bottoms that comprises MAS, at least some DAS, and at least about 20 wt % water, cooling and/or evaporating the first bottoms, and optionally adding an antisolvent to the bottoms, to attain a temperature and composition sufficient to cause the first bottoms to separate into a DAS-containing liquid portion and a MAS-containing first solid portion that is substantially free of DAS, separating the first solid portion from the first liquid portion, recovering the first solid portion, dissolving the first solid portion in water to produce an aqueous MAS solution, distilling the aqueous MAS solution at a temperature and pressure sufficient to form a second overhead that comprises water and ammonia, and a second bottoms that comprises a major portion of SA, a minor portion of MAS, and water, cooling the second bottoms to cause the second bottoms to separate into a second liquid portion in contact with a second solid portion that consists essentially of SA and is substantially free of MAS, separating the second solid portion from the second liquid portion, recovering the second solid portion, hydrogenating the second solid portion in the presence of at least one hydrogenation catalyst to produce the hydrogenated product comprising at least one of THF, GBL or BDO, and recovering the hydrogenated product.

We also provide a process for making a hydrogenated product including providing a clarified SA-containing fermentation broth, optionally, adding at least one of MAS, DAS, SA, $NH_3$ and $NH_4^+$ to the broth to maintain the pH of the broth below 6, distilling the broth to form an overhead that comprises water and ammonia, and a liquid bottoms that includes MAS, at least some DAS, and at least about 20 wt % water, cooling and/or evaporating the bottoms, and optionally adding an antisolvent to the bottoms, to attain a temperature and composition sufficient to cause the bottoms to separate into a DAS-containing liquid portion and a MAS-containing solid portion that is substantially free of DAS, separating the solid portion from the liquid portion, recovering the solid portion, dissolving the solid portion in water to produce an aqueous MAS solution, distilling the aqueous MAS solution at a temperature and pressure sufficient to form a second overhead that comprises water and ammonia, and a second bottoms that comprises a major portion of SA, a minor portion of MAS, and water, cooling and/or evaporating the second bottoms to cause the second bottoms to separate into a second liquid portion and a second solid portion that consists essentially of SA and is substantially free of MAS, separating the second solid portion from the second liquid portion, recovering the second solid portion, hydrogenating the second solid portion in the presence of at least one hydrogenation catalyst to produce the hydrogenated product comprising at least one of THF, GBL or BDO, and recovering the hydrogenated product.

We further provide a process for a hydrogenated product including providing making a DAS-containing fermentation broth, distilling the broth to form a first overhead that includes water and ammonia, and a first liquid bottoms that includes MAS, at least some DAS, and at least about 20 wt % water, cooling and/or evaporating the bottoms, and optionally adding an antisolvent to the bottoms, to attain a temperature and composition sufficient to cause the bottoms to separate into a DAS-containing liquid portion and a MAS-containing solid portion that is substantially free of DAS, separating the solid portion from the liquid portion, recovering the solid portion, dissolving the solid portion in water to produce an aqueous MAS solution, distilling the aqueous MAS solution at a temperature and pressure sufficient to form a second overhead that includes water and ammonia, and a second bottoms that includes a major portion of SA, a minor portion of MAS, and water, cooling and/or evaporating the second bottoms to cause the second bottoms to separate into a second liquid portion in contact with a second solid portion that preferably consists essentially of SA and is substantially free of MAS, separating the second solid portion from the second liquid portion, recovering the second solid portion, hydrogenating the second solid portion in the presence of at least one hydrogenation catalyst to produce the hydrogenated product comprising at least one of THF, GBL or BDO, and recovering the hydrogenated product.

We further provide a process for making a hydrogenated product including providing a clarified MAS-containing broth, optionally, adding at least one of MAS, DAS, SA, $NH_3$ and $NH_4^+$ to the broth to preferably maintain the pH of the broth below 6, distilling the broth to form an overhead that includes water and optionally ammonia, and a liquid bottoms that includes MAS, at least some DAS, and at least about 20 wt % water, cooling and/or evaporating the bottoms, and optionally adding an antisolvent to the bottoms, to attain a temperature and composition sufficient to cause the bottoms to separate into a DAS-containing liquid portion and a MAS-containing solid portion that is substantially free of DAS, separating the solid portion from the liquid portion, recovering the solid portion, hydrogentating the solid portion in the presence of at least one hydrogenation catalyst to produce the hydrogenated product comprising at least one of THF, GBL or BDO, and recovering the hydrogenated product.

DETAILED DESCRIPTION

Figure 1:
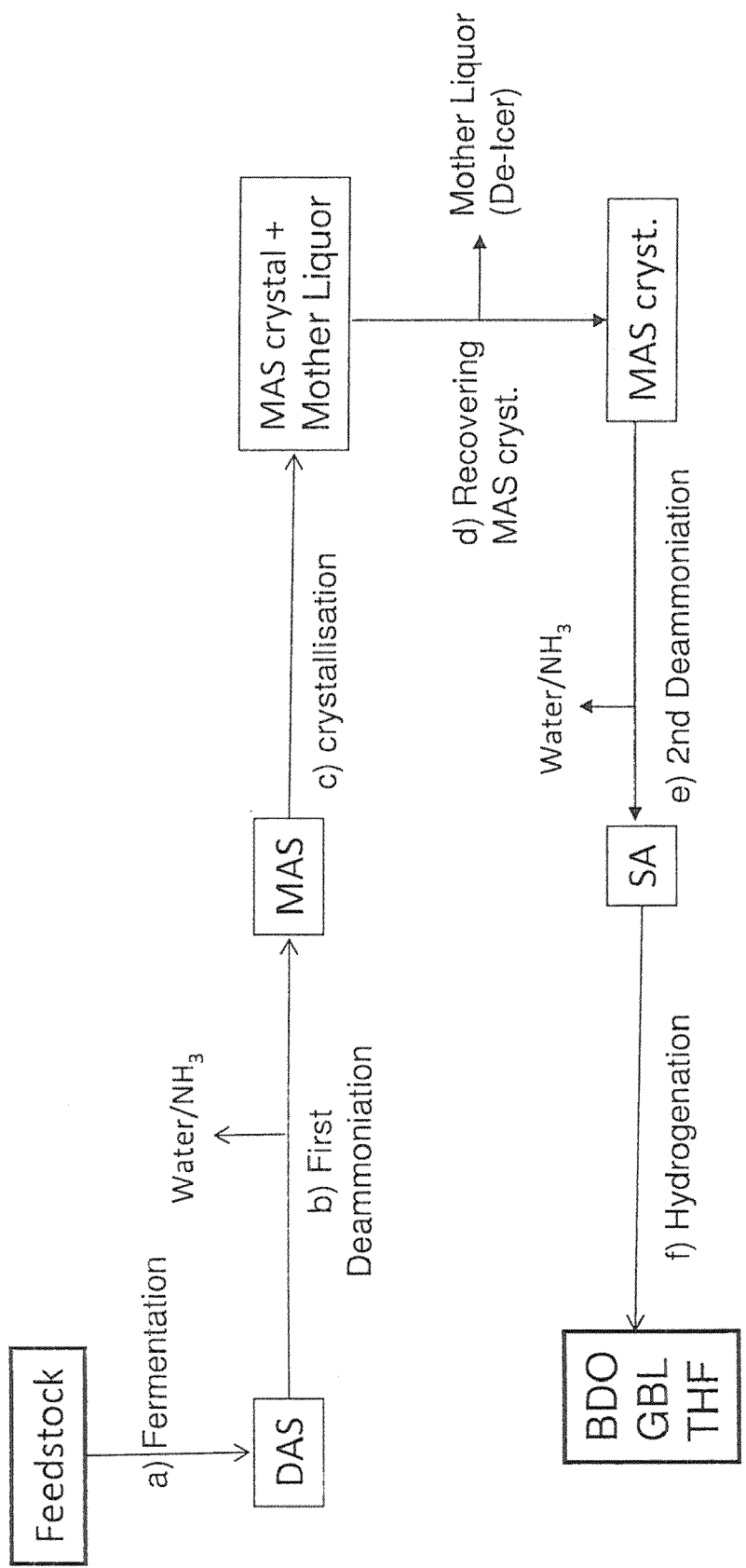
FIG. 1 schematically illustrates a fully integrated process for hydrogenation of fermentation-derived SA to BDO, THF, and GBL and depicts two-stage deammoniation of DAS with a MAS crystallization step between the two stages.

It will be appreciated that at least a portion of the following description is intended to refer to representative examples of processes selected for illustration in the drawings and is not intended to define or limit the disclosure, other than in the appended claims.

Our processes may be appreciated by reference to FIG. 1, which shows in block diagram form one representative example of our methods.

A growth vessel, typically at in-place steam sterilizable fermentor, may be used to grow a microbial culture (not shown) that is subsequently utilized for the production of the DAS, MAS, and/or SA-containing fermentation broth. Such growth vessels are known in the art and are not further discussed.

The microbial culture may comprise microorganisms capable of producing SA from fermentable carbon sources such as carbohydrate sugars. Representative examples of microorganisms include, but are not limited to, *Escherichia coli* (*E. coli*), *Aspergillus niger*, *Corynebacterium glutamicum* (also called *Brevibacterium flavum*), *Enterococcus faecalis*, *Veillonella parvula*, *Actinobacillus succinogenes*, *Mannheimia succiniciproducens*, *Anaerobiospirillum succiniciproducens*, *Paecilomyces Varioti*, *Saccharomyces cerevisiae*, *Bacteroides fragilis*, *Bacteroides ruminicola*, *Bacteroides amylophilus*, *Alcaligenes eutrophus*, *Brevibacterium ammoniagenes*, *Brevibacterium lactofermentum*, *Candida brumptii*, *Candida catenulate*, *Candida mycoderma*, *Candida zeylanoides*, *Candida paludigena*, *Candida sonorensis*, *Candida utilis*, *Candida zeylanoides*, *Debaryomyces hansenii*, *Fusarium oxysporum*, *Humicola lanuginosa*, *Kloeckera apiculata*, *Kluyveromyces lactis*, *Kluyveromyces wickerhamii*, *Penicillium simplicissimum*, *Pichia anomala*, *Pichia besseyi*, *Pichia media*, *Pichia guilliermondii*, *Pichia inositovora*, *Pichia stipidis*, *Saccharomyces bayanus*, *Schizosaccharomyces pombe*, *Torulopsis candida*, *Yarrowia lipolytica*, mixtures thereof and the like.

A preferred microorganism is an *E. coli* strain deposited at the ATCC under accession number PTA-5132. More preferred is this strain with its three antibiotic resistance genes (cat, amphl, tetA) removed. Removal of the antibiotic resistance genes cat (coding for the resistance to chloramphenicol), and amphl (coding for the resistance to kanamycin) can be performed by the so-called "Lambda-red (λ-red)" procedure as described in Datsenko K A and Wanner B L., Proc. Natl. Acad. Sci. USA 2000 Jun. 6; 97(12) 6640-5, the subject matter of which is incorporated herein by reference. The tetracycline resistant gene tetA can be removed using the procedure originally described by Bochner et al., J. Bacteriol. 1980 August; 143(2): 926-933, the subject matter of which is incorporated herein by reference. Glucose is a preferred fermentable carbon source for this microorganism.

A fermentable carbon source (e.g., carbohydrates and sugars), optionally a source of nitrogen and complex nutrients (e.g., corn steep liquor), additional media components such as vitamins, salts and other materials that can improve cellular growth and/or product formation, and water may be fed to the growth vessel for growth and sustenance of the microbial culture. Typically, the microbial culture is grown under aerobic conditions provided by sparging an oxygen-rich gas (e.g., air or the like). Typically, an acid (e.g., sulphuric acid or the like) and ammonium hydroxide are provided for pH control during the growth of the microbial culture.

In one example (not shown), the aerobic conditions in the growth vessel (provided by sparging an oxygen-rich gas) are switched to anaerobic conditions by changing the oxygen-rich gas to an oxygen-deficient gas (e.g., $CO_2$ or the like). The anaerobic environment triggers bioconversion of the fermentable carbon source to SA in situ in the growth vessel. Ammonium hydroxide is provided for pH control during bioconversion of the fermentable carbon source to SA. The SA that is produced is at least partially neutralized to DAS due to the presence of the ammonium hydroxide, leading to the production of a broth comprising DAS. The $CO_2$ provides an additional source of carbon for the production of SA.

In another example, the contents of the growth vessel may be transferred via a stream to a separate bioconversion vessel for bioconversion of a carbohydrate source to SA. An oxygen-deficient gas (e.g., $CO_2$ or the like) is sparged in the bioconversion vessel to provide anaerobic conditions that trigger production of SA. Ammonium hydroxide is provided for pH control during bioconversion of the carbohydrate source to SA. Due to the presence of the ammonium hydroxide, the SA produced is at least partially neutralized to DAS, leading to production of a broth that comprises DAS. The $CO_2$ provides an additional source of carbon for production of SA.

In yet another example, the bioconversion may be conducted at relatively low pH (e.g., 3-6). A base (ammonium hydroxide or ammonia) may be provided for pH control during bioconversion of the carbohydrate source to SA. Depending on the desired pH, due to the presence or lack of the ammonium hydroxide, either SA is produced or the SA produced is at least partially neutralized to MAS, DAS, or a mixture comprising SA, MAS and/or DAS. Thus, the SA produced during bioconversion can be subsequently neutralized, optionally in an additional step, by providing either ammonia or ammonium hydroxide leading to a broth comprising DAS. As a consequence, a "DAS-containing fermentation broth" generally means that the fermentation broth comprises DAS and possibly any number of other components such as MAS and/or SA, whether added and/or produced by bioconversion or otherwise. Similarly, a "MAS-containing fermentation broth" generally means that the fermentation broth comprises MAS and possibly any number of other components such as DAS and/or SA, whether added and/or produced by bioconversion or otherwise.

The broth resulting from the bioconversion of the fermentable carbon source (in either the vessel or the stream, depending on where the bioconversion takes place), typically contains insoluble solids such as cellular biomass and other suspended material, which are transferred via a stream to a clarification apparatus before distillation. Removal of insoluble solids clarifies the broth. This reduces or prevents fouling of subsequent distillation equipment. The insoluble solids can be removed by any one of several solid-liquid separation techniques, alone or in combination, including but not limited to, centrifugation and filtration (including, but not limited to ultra-filtration, micro-filtration or depth filtration). The choice of filtration can be made using techniques known in the art. Soluble inorganic compounds can be removed by any number of known methods such as, but not limited to, ion-exchange, physical adsorption and the like.

An example of centrifugation is a continuous disc stack centrifuge. It may be useful to add a polishing filtration step following centrifugation such as depth filtration, which may include the use of a filter aide such as diatomaceous earth or the like, or more preferably ultra-filtration or micro-filtration. The ultra-filtration or micro-filtration membrane can be ceramic or polymeric, for example. One example of a polymeric membrane is SelRO MPS-U20P (pH stable ultra-filtration membrane) manufactured by Koch Membrane Systems (850 Main Street, Wilmington, Mass., USA). This is a commercially available polyethersulfone membrane with a 25,000 Dalton molecular weight cut-off which typically operates at pressures of 0.35 to 1.38 MPa (maximum pressure of 1.55 MPa) and at temperatures up to 50 C. Alternatively, a filtration step may be employed, such as ultra-filtration or micro-filtration alone.

The resulting clarified DAS-containing broth or MAS-containing broth, substantially free of the microbial culture and other solids, is transferred via a stream to a distillation apparatus.

The clarified distillation broth should contain DAS and/or MAS in an amount that is at least a majority of, preferably at least about 70 wt %, more preferably 80 wt % and most preferably at least about 90 wt % of all the diammonium dicarboxylate salts in the broth. The concentration of DAS as a weight percent (wt %) of the total dicarboxylic acid salts in the fermentation broth can be easily determined by high pressure liquid chromatography (HPLC) or other known means.

Water and ammonia are removed from the distillation apparatus as an overhead, and at least a portion is optionally recycled via a stream to the bioconversion vessel (or the growth vessel operated in the anaerobic mode). Distillation temperature and pressure are not critical as long as the distillation is carried out in a way that ensures that the distillation overhead contains water and ammonia, and the distillation bottoms comprises at least some DAS and at least about 20 wt % water. A more preferred amount of water is at least about 30 wt % and an even more preferred amount is at least about 40 wt %. The rate of ammonia removal from the distillation step increases with increasing temperature and also can be increased by injecting steam (not shown) during distillation. The rate of ammonia removal during distillation may also be increased by conducting distillation under a vacuum or by sparging the distillation apparatus with a non-reactive gas such as air, nitrogen or the like.

Removal of water during the distillation step can be enhanced by the use of an organic azeotroping agent such as toluene, xylene, hexane, cyclohexane, methyl cyclohexane, methyl isobutyl ketone, heptane or the like, provided that the bottoms contains at least about 20 wt % water. If the distillation is carried out in the presence of an organic agent capable of forming an azeotrope consisting of the water and the agent, distillation produces a biphasic bottoms that comprises an aqueous phase and an organic phase, in which case the aqueous phase can be separated from the organic phase, and the aqueous phase used as the distillation bottoms. Byproducts such as succinamide and succinimide are substantially avoided provided the water level in the bottoms is maintained at a level of at least about 30 wt %.

A preferred temperature for the distillation step is in the range of about 50 to about 300° C., depending on the pressure. A more preferred temperature range is about 90 to about 150° C., depending on the pressure. A distillation temperature of about 110 to about 140° C. is preferred. "Distillation temperature" refers to the temperature of the bottoms (for batch distillations this may be the temperature at the time when the last desired amount of overhead is taken).

Adding a water miscible organic solvent or an ammonia separating solvent facilitates deammoniation over a variety of distillation temperatures and pressures as discussed above. Such solvents include aprotic, bipolar, oxygen-containing solvents that may be able to form passive hydrogen bonds. Examples include, but are not limited to, diglyme, triglyme, tetraglyme sulfoxides such as dimethylsulfoxide (DMSO), amides such as dimethylformamide (DMF) and dimethylacetamide, sulfones such as dimethylsulfone, sulfolane, GBL, polyethyleneglycol (PEG), butoxytriglycol, N-methylpyrolidone (NMP), ethers such as dibutylether, dioxane, diethyleneglycoldimethylether, methyl isobutyl ketone (MIBK), methyl ethyl ketone (MEK) and the like. Such solvents aid in the removal of ammonia from the DAS or MAS in the clarified broth. Regardless of the distillation technique, it is important that the distillation be carried out in a way that ensures that at least some DAS and at least about 20 wt % water remain in the bottoms and even more advantageously at least about 30 wt %.

The distillation can be performed at atmospheric, sub-atmospheric or super-atmospheric pressures. The distillation can be a one-stage flash, a multistage distillation (i.e., a multistage column distillation) or the like. The one-stage flash can be conducted in any type of flasher (e.g., a wiped film evaporator, thin film evaporator, thermosiphon flasher, forced circulation flasher and the like). The multistages of the distillation column can be achieved by using trays, packing or the like. The packing can be random packing (e.g., Raschig rings, Pall rings, Berl saddles and the like) or structured packing (e.g., Koch-Sulzer packing, Intalox packing, Mellapak and the like). The trays can be of any design (e.g., sieve trays, valve trays, bubble-cap trays and the like). The distillation can be performed with any number of theoretical stages.

If the distillation apparatus is a column, the configuration is not particularly critical, and the column can be designed using well known criteria. The column can be operated in either stripping mode, rectifying mode or fractionation mode. Distillation can be conducted in either batch or continuous mode. In the continuous mode, the broth may be fed continuously into the distillation apparatus, and the overhead and bottoms continuously removed from the apparatus as they are formed. The distillate from distillation is an ammonia/water solution, and the distillation bottoms is a liquid, aqueous solution of MAS and DAS, which may also contain other fermentation by-product salts (i.e., ammonium acetate, ammonium formate, ammonium lactate and the like) and color bodies.

The distillation bottoms can be transferred via a stream to a cooling apparatus and cooled by conventional techniques. Cooling technique is not critical, although a preferred technique will be described below. A heat exchanger (with heat recovery) can be used. A flash vaporization cooler can be used to cool the bottoms down to about 15° C. Cooling to 0° C. typically employs a refrigerated coolant such as, for example, glycol solution or, less preferably, brine. A concentration step can be included prior to cooling to help increase product yield. Further, both concentration and cooling can be combined using methods known such as vacuum evaporation and heat removal using integrated cooling jackets and/or external heat exchangers.

Figure 3:
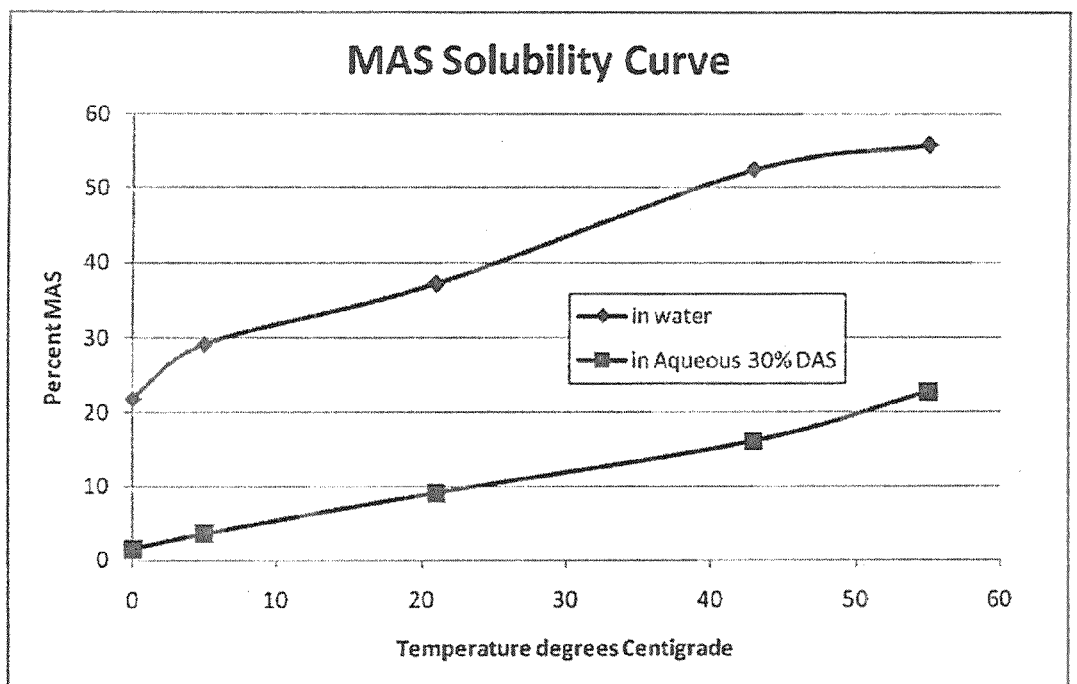
FIG. 3 is a graph showing the solubility of MAS as a function of temperature in both water and a 30% aqueous DAS solution.

We found that the presence of some DAS in the liquid bottoms facilitates cooling-induced separation of the bottoms into a liquid portion in contact with a solid portion that at least "consists essentially" of MAS (meaning that the solid portion is at least substantially pure crystalline MAS) by reducing the solubility of MAS in the liquid, aqueous, DAS-containing bottoms. FIG. 3 illustrates the reduced solubility of MAS in an aqueous 30 wt % DAS solution at various temperatures ranging from 0 to 60° C. The upper curve shows that even at 0° C. MAS remains significantly soluble in water (i.e., about 20 wt % in aqueous solution). The lower curve shows that at 0° C. MAS is essentially insoluble in a 30 wt % aqueous DAS solution. We discovered, therefore, that MAS can be more completely crystallized out of an aqueous solution if some DAS is also present in that solution. A preferred concentration of DAS in such a solution is about 30 wt % or higher. This phenomenon allows crystallization of MAS (i.e., formation of the solid portion of the distillation bottoms) at temperatures higher than those that would be required in the absence of DAS.

When 50% of the ammonia is removed from DAS contained in an aqueous medium the succinate species establish an equilibrium molar distribution that is about 0.1:0.8:0.1 in DAS:MAS:SA within a pH range of 4.8 to 5.4, depending on the operating temperature and pressure. When this composition is concentrated and cooled, MAS exceeds its solubility limit in water and crystallizes. When MAS undergoes a phase change to the solid phase, the liquid phase equilibrium resets thereby producing more MAS (DAS donates an ammonium ion to SA). This causes more MAS to crystallize from solution and continues until appreciable quantities of SA are exhausted and the pH tends to rise. As the pH rises, the liquid phase distribution favors DAS. However, since DAS is highly soluble in water, MAS continues to crystallize as its solubility is lower than DAS. In effect, the liquid phase equilibrium and the liquid-solid equilibria of succinate species act as a "pump" for MAS crystallization, thereby enabling MAS crystallization in high yield.

In addition to cooling, evaporation, or evaporative cooling described above, crystallization of MAS can be enabled and/or facilitated by addition of an antisolvent. In this context, antisolvents may be solvents typically miscible with water but cause crystallization of a water soluble salt such as MAS due to lower solubility of the salt in the solvent. Solvents with an antisolvent effect on MAS can be alcohols such as ethanol and propanol, ketones such as methyl ethyl ketone, ethers such as tetrahydrofuran and the like. The use of antisolvents is known and can be used in combination with cooling and evaporation or separately.

The distillation bottoms may be fed via a stream to a separator for separation of the solid portion from the liquid portion. Separation can be accomplished via pressure filtration (e.g., using Nutsche or Rosenmond type pressure filters), centrifugation and the like. The resulting solid product can be recovered as a product and dried, if desired, by standard methods.

After separation, it may be desirable to treat the solid portion to ensure that no liquid portion remains on the surface (s) of the solid portion. One way to minimize the amount of liquid portion that remains on the surface of the solid portion is to wash the separated solid portion with water and dry the resulting washed solid portion. A convenient way to wash the solid portion is to use a so-called "basket centrifuge." Suitable basket centrifuges are available from The Western States Machine Company (Hamilton, Ohio, USA).

The liquid portion of the separator (i.e., the mother liquor) may contain remaining dissolved MAS, any unconverted DAS, any fermentation byproducts such as ammonium acetate, lactate, or formate, and other minor impurities. This liquid portion can be fed via a stream to a downstream apparatus. In one instance, the downstream apparatus may be a means for making a de-icer by treating in the mixture with an appropriate amount of potassium hydroxide, for example, to convert the ammonium salts to potassium salts. Ammonia generated in this reaction can be recovered for reuse in the bioconversion vessel (or the growth vessel operating in the anaerobic mode). The resulting mixture of potassium salts is valuable as a de-icer and anti-icer.

The mother liquor from the solids separation step, can be recycled (or partially recycled) to the distillation apparatus via a stream to further enhance recovery of MAS, as well as further convert DAS to MAS.

The solid portion of the cooling-induced crystallization is substantially pure MAS and is, therefore, useful for the known utilities of MAS.

HPLC can be used to detect the presence of nitrogen-containing impurities such as succinamide and succinimide. The purity of MAS can be determined by elemental carbon and nitrogen analysis. An ammonia electrode can be used to determine a crude approximation of MAS purity.

Depending on the circumstances and various operating inputs, there are instances when the fermentation broth may be a clarified MAS-containing fermentation broth or a clarified SA-containing fermentation broth. In those circumstances, it can be advantageous to optionally add MAS, DAS, SA, ammonia and/or ammonium hydroxide to those fermentation broths to facilitate the production of substantially pure MAS. For example, the operating pH of the fermentation broth may be oriented such that the broth is a MAS-containing broth or a SA-containing broth. MAS, DAS, SA, ammonia and/or ammonium hydroxide may be optionally added to those broths to attain a broth pH preferably <6 to facilitate production of the above-mentioned substantially pure MAS. Also, it is possible that MAS, DAS and/or SA from other sources may be added as desired. In one particular form, it is especially advantageous to recycle MAS, DAS and water from the liquid bottoms resulting from the distillation step into the fermentation broth. In referring to the MAS-containing broth, such broth generally means that the fermentation broth comprises MAS and possibly any number of other components such as DAS and/or SA, whether added and/or produced by bioconversion or otherwise.

The solid portion can be converted into SA by removing ammonia. This can be carried out as follows. The solid portion (consisting essentially of MAS) obtained from any of the above-described conversion processes can be dissolved in water to produce an aqueous MAS solution. This solution can then be distilled at a temperature and pressure sufficient to form an overhead that comprises water and ammonia, and a bottoms that comprises a major portion of SA, a minor portion of MAS and water. The bottoms can be cooled to cause it to separate into a liquid portion in contact with a solid portion that consists essentially of SA and is substantially free of MAS. The solid portion can be separated from the second liquid portion and recovered as substantially pure SA as determined by HPLC.

Figure 4:
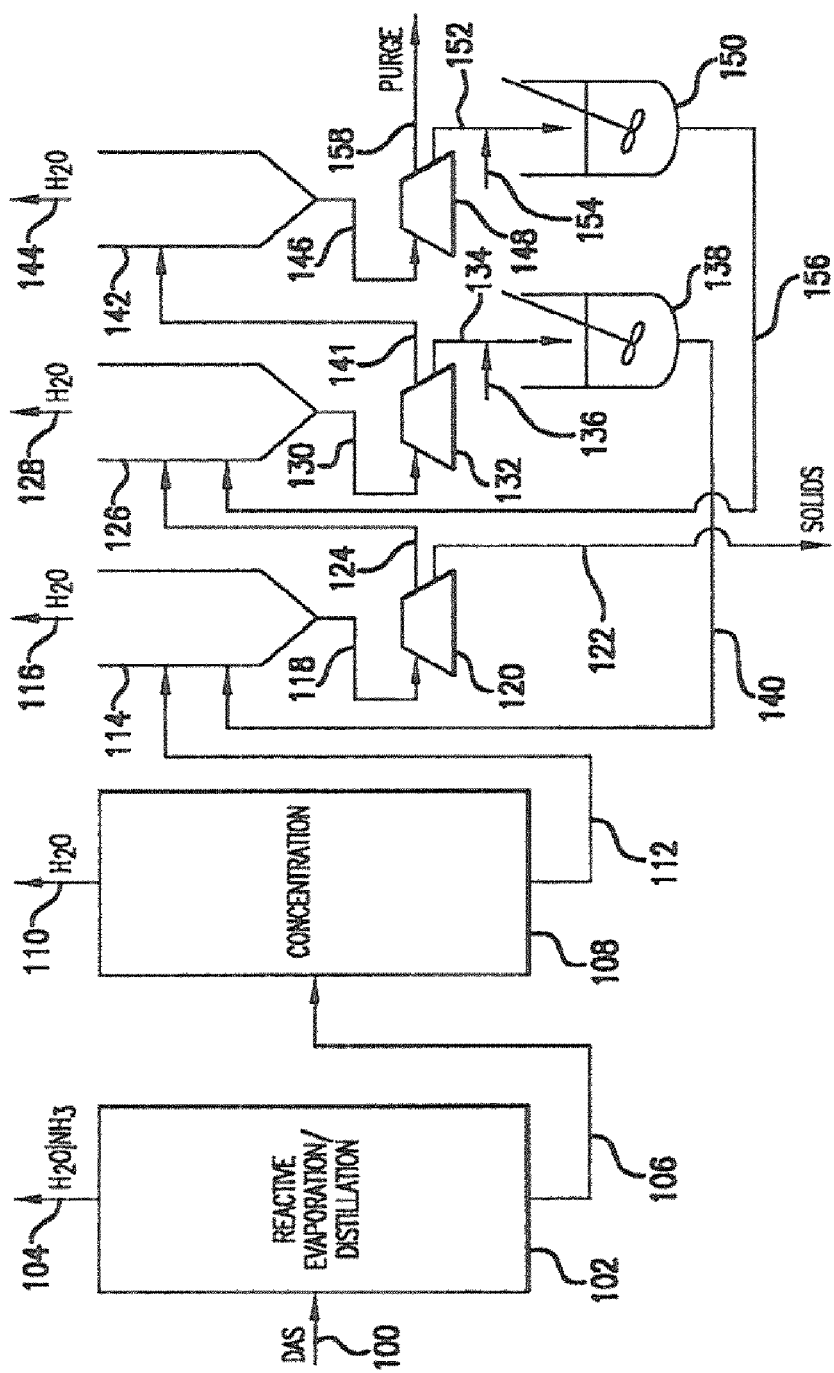
FIG. 4 is a flow diagram showing selected aspects of our process.

Turning to FIG. 4, we describe one of our particularly preferred processes. In FIG. 4, a stream 100 of DAS, which may be a stream of clarified fermentation broth which contains DAS (among other things), is subjected to reactive evaporation/distillation in distillation column 102. The distillation may occur over a range of temperatures such as about 110 to about 145° C., preferably about 135° C. The pressure in the distillation column 102 can be over a broad range about 1.5-about 4 bar, preferably about 3.5 bar. Water and ammonia are separated in distillation column 102 and form an overhead 104. The liquid bottoms 106 comprises MAS, at least some DAS and at least about 20 wt % water. Typically, bottoms 106 contains about 5-about 20 wt % MAS, about 80 wt %-about 95 wt % water and about 1-about 3 wt % DAS. The pH of the bottoms may be in a range of about 4.6-about 5.6.

The bottoms 106 is streamed to a concentrator 108 which removes water via overhead stream 110. Concentrator 108 can operate over a range of temperatures such as about 90° C.-about 110° C., preferably about 100° C. and over a range of pressures such as at about 0.9 bar-about 1.2 bar, preferably about 1.103 bar.

Concentrator 108 produces a bottoms stream 112 which typically contains about 40 wt %-about 70 wt %, preferably about 55 wt % MAS. Hence, the concentrator concentrates the amount of MAS typically by about 2-about 11 times, preferably about 4 times-about 6 times.

Bottoms stream 112 flows to a first crystallizer 114 which operates at a temperature typically at about 50 to about 70° C., preferably about 60° C. A water overhead stream 116 is produced by the crystallizer. Bottoms 118 flows to a centrifuge 120 which produces a solid stream 122 which typically has a yield of MAS of about 95%. A remaining liquid flow 124 is sent to a second crystallizer 126 which removes additional water by way of overhead stream 128 and operates at a temperature typically at about 30 to about 50° C., preferably about 40° C. The bottoms stream 130 flows to a centrifuge 132. Centrifuge produces a solid stream 134 which is redissolved with a water stream 136 which introduces water in a temperature range typically of about 70 to about 90° C., preferably about 90° C. That stream flows to a first mixer 138 and produces a first recycle flow 140 back to the first crystallizer 114.

Remaining liquid from centrifuge 132 flows via stream 141 to third crystallizer 142 which produces an overhead stream 144 of water. Third crystallizer 132 typically operates at a temperature of about 10 to about 30° C., typically about 20° C. The remaining bottoms flow 146 streams to a third centrifuge 148 and solid material produced by third centrifuge 148 flows to a second mixer 150 by way of stream 152. That solid stream is dissolved by a second water stream 154 which introduces water typically at a temperature range of about 50 to about 70° C., preferably about 70° C. Second mixer 150 produces a recycle stream 156 which is recycled to second crystallizer 126. Remaining material flows outwardly of the system from third centrifuge 148 by way of purge stream 158 which typically represents about 5 wt % of the total MAS contained in stream 112. It is understood that the desired crystallization temperatures in crystallizers 114, 126, and 142 can be attained by evaporation (as depicted), or by indirect contact with an external cooling medium, or a combination thereof.

Figure 5:
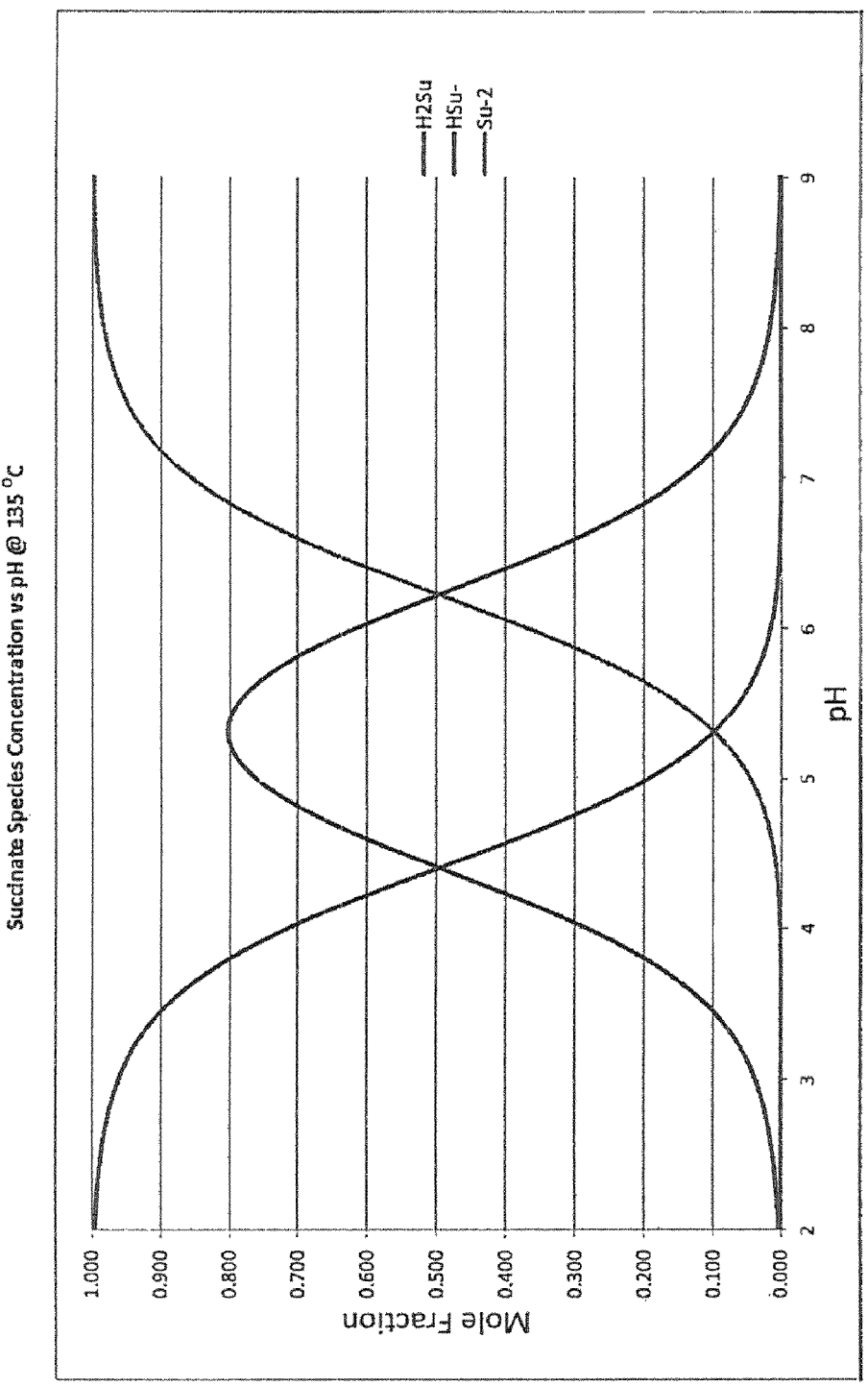
FIG. 5 is a graph showing the mole fraction of MAS (Hsu-), DAS (Su-2), and SA (H2Su) as a function of pH at 135° C.
Figure 6:
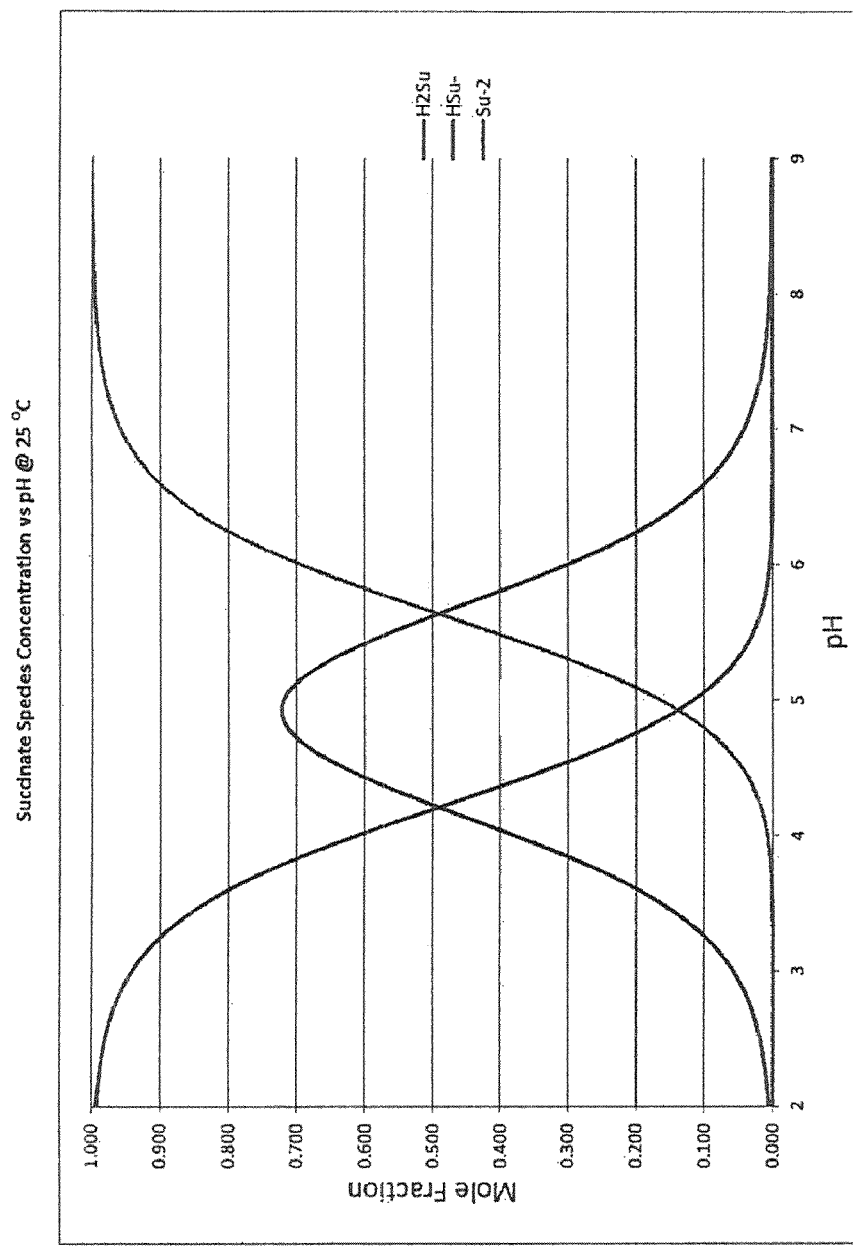
FIG. 6 is a graph similar to that of FIG. 5 at 25° C.

FIG. 5 is a graph showing the mole fraction of MAS, DAS and SA as a function of pH at 135° C., which is typical of the temperature in distillation column 102 of FIG. 4. FIG. 6 is the same as FIG. 5 except for a temperature at 25° C. Those figures show the relative proportions of the three components depending on the pH at the particular temperature. In accordance with our methods, the typical operating pH of the reactive evaporation/distillation unit 102 and the concentration unit 108 may be about 5.3 leading to maximum production of MAS. When 50% of the ammonia is removed from DAS contained in an aqueous medium the succinate species establish an equilibrium molar distribution that is about 0.1: 0.8:0.1 in DAS:MAS:SA within a pH range of about 4.8 to about 5.4, depending on the operating temperature and pressure. Without being bound by any particular theory, we believe that when this composition is concentrated and cooled, MAS exceeds its solubility limit in water and crystallizes. Also, when MAS undergoes a phase change to the solid phase, the liquid phase equilibrium is believed to deliberately reset, thereby producing more MAS (DAS donates an ammonium ion to SA). We believe that this causes more MAS to crystallize from solution and continues until appreciable quantities of SA are exhausted and the pH tends to rise. As the pH rises, the liquid phase distribution favors DAS. However, since DAS is highly soluble in water, MAS continues to crystallize as its solubility is lower than DAS. In effect, the liquid phase equilibrium and the liquid-solid equilibria of succinate species act as a "pump" for MAS crystallization, thereby enabling MAS crystallization in high yield.

Figure 7:
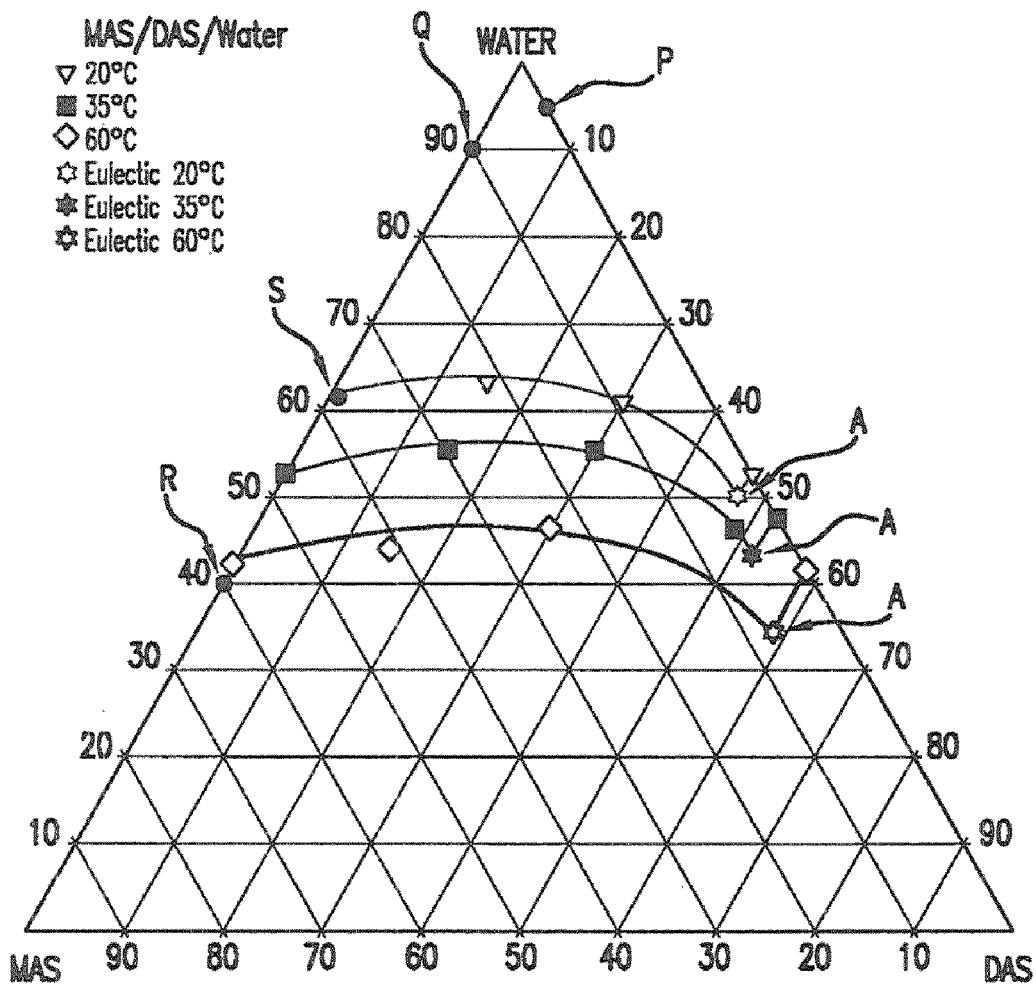
FIG. 7 is a ternary diagram of MAS, DAS and water at selected temperatures.

FIG. 7 is a ternary diagram of MAS, DAS and water at three different temperatures, namely 20° C., 35° C. and 60° C. This diagram is illustrative of the solid-liquid equilibrium that causes crystallization of pure MAS or DAS at different temperatures. We constructed FIG. 7 with experimental solubility data which shows that if a liquid composition containing MAS, DAS, and water is cooled to cause the separation of a solid portion and if the liquid composition lies to the left of the eutectic points identified as "A," then liquid-solid equilibrium principles suggest that the solid portion will be pure MAS. Conversely, if a liquid composition containing MAS, DAS, and water is cooled to cause the separation of a solid portion and if the liquid composition lies to the right of the eutectic points identified as "A," then liquid-solid equilibrium principles suggest that the solid portion will be pure DAS. Our processes, depicted representatively in FIG. 4, are designed to operate to the left of the eutectic points identified as "A" and, therefore, are expected to produce pure MAS.

Henceforth, representative processes are described with respect to FIGS. 4 and 7. Typically, stream 100 is representative of point "P," which is a DAS containing broth at about 5 wt %. In the reactive evaporation/distillation step 102, water and ammonia are evaporated/distilled to form a 10 wt % MAS containing solution, typically, which is represented by point "Q." Subsequently, in the concentration unit 108, the MAS containing solution is concentrated to form a 60 wt % MAS containing solution, typically, which is represented by point "R." Finally, the 60 wt % MAS containing solution is cooled (by evaporation, indirect contact cooling, or by a combination thereof) to produce an approximately 37 wt % MAS containing liquid portion represented by point "S" in contact with a solid portion. According to liquid-solid equilibrium principles, our FIG. 7 shows that the solid portion will be essentially pure MAS that is substantially free of DAS since we typically operate our processes to the left of the eutectic points.

Figure 8:
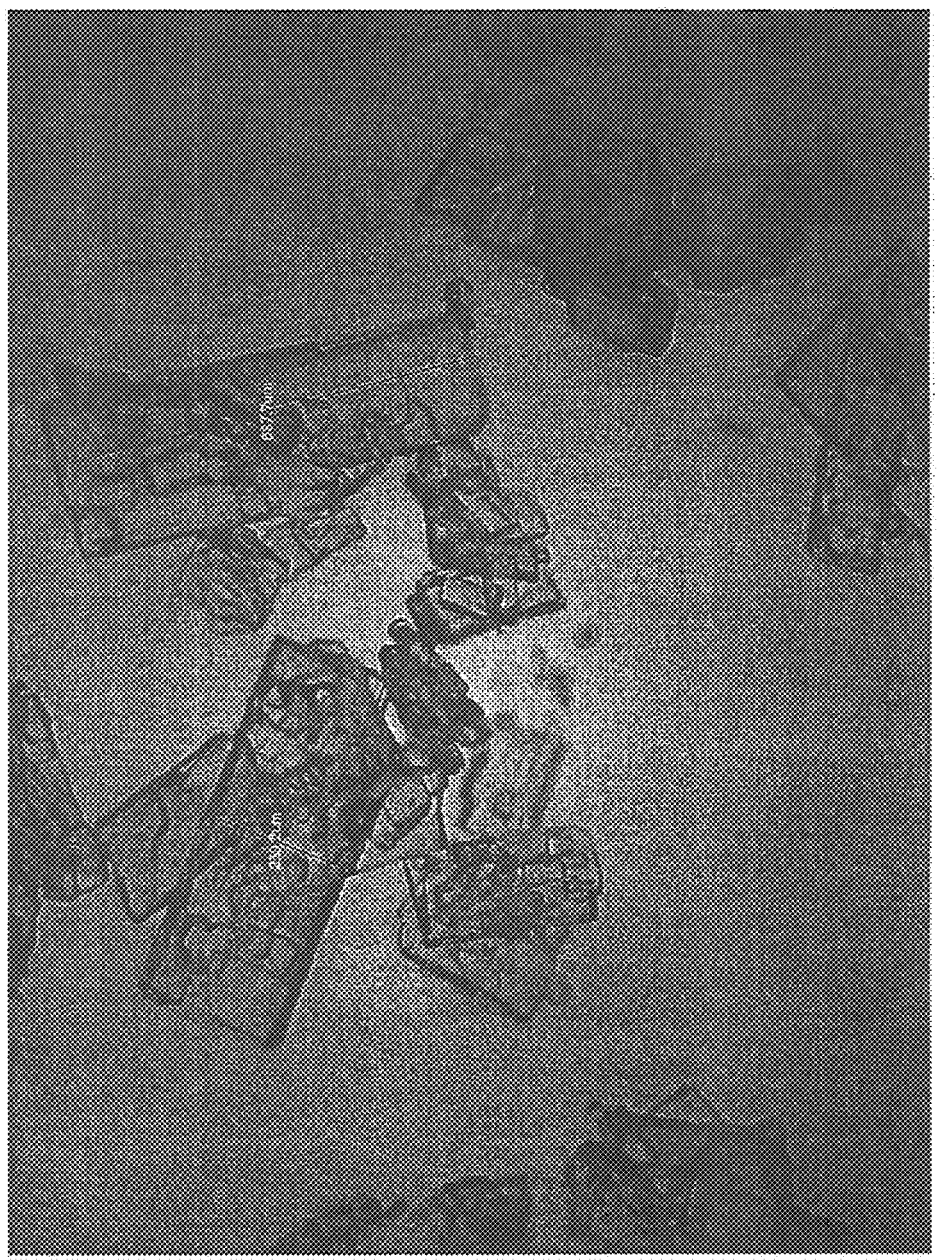
FIG. 8 is a microphotograph of MAS crystals produced by our methods.
Figure 9:
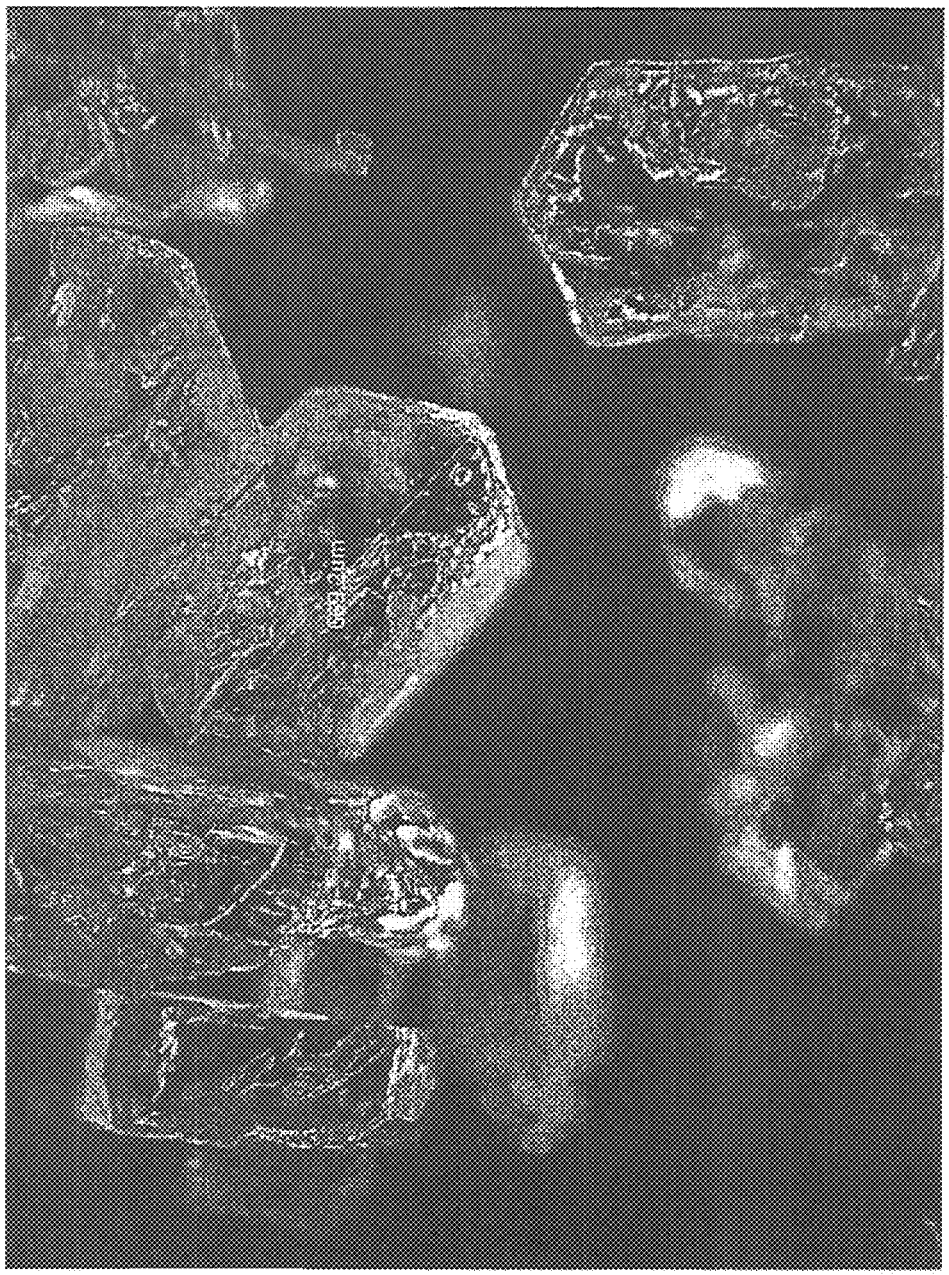
FIG. 9 is a microphotograph of SA crystals produced by our methods.

FIG. 8 is a microphotograph showing representative MAS crystals produced in accordance with our methods. Similarly, FIG. 9 is a microphotograph of representative SA crystals produced in accordance with our methods. The micrographs demonstrate that MAS has a crystal shape that is distinct from that of SA. Henceforth, we have shown that we can produce essentially pure MAS that is both substantially free of DAS and SA using our methods.

The SA may be dissolved in water to form an aqueous solution of SA which can be fed directly to a hydrogenation reactor. The preferred concentration of SA in the feed solution is about 4% to about 50% and more preferably about 4% to about 10%.

Figure 2:
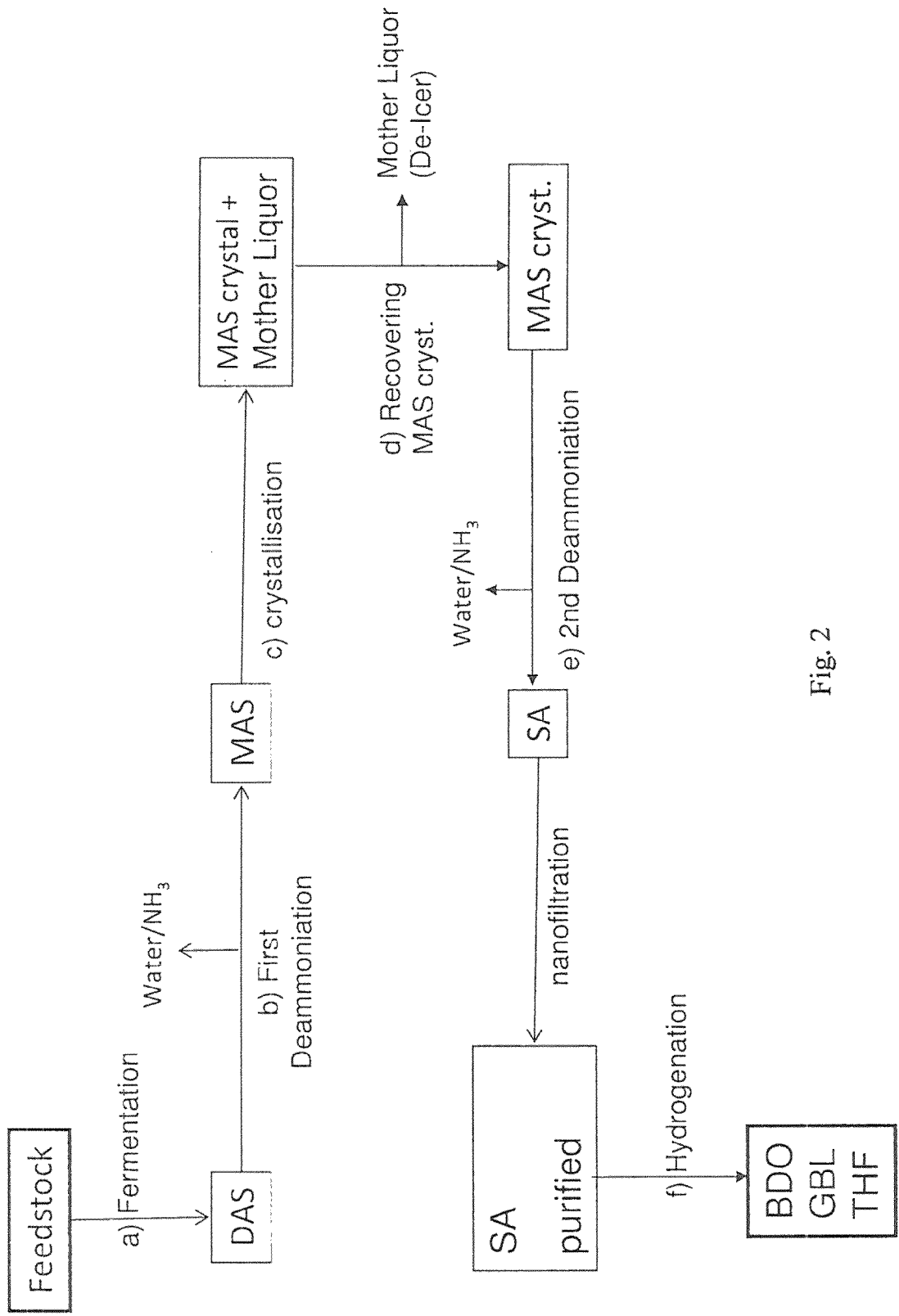
FIG. 2 schematically illustrates a fully integrated process for hydrogenation of fermentation-derived SA to BDO, THF, and GBL and depicts two-stage deammoniation of DAS with a MAS crystallization step between the two stages. An optional nanofiltration step is included for additional purification of SA prior to hydrogenation.

The SA solution can be further purified using nanofiltration as schematically shown in FIG. 2. Surprisingly, we observed that nanofiltration is useful in filtering out fermentation-derived impurities such as polypeptides and polysaccharides that could impair the performance of structured hydrogenation catalysts.

Streams comprising SA such as those presented in FIGS. 1 and 2 may be contacted with hydrogen and a hydrogenation catalyst at elevated temperatures and pressures to produce a hydrogenation product comprising THF, BDO and GBL.

A principal component of the catalyst useful for hydrogenation of SA may be at least one metal from palladium, ruthenium, rhenium, rhodium, iridium, platinum, nickel, cobalt, copper, iron and compounds thereof.

A chemical promoter may augment the activity of the catalyst. The promoter may be incorporated into the catalyst during any step in the chemical processing of the catalyst constituent. The chemical promoter generally enhances the physical or chemical function of the catalyst agent, but can also be added to retard undesirable side reactions. Suitable promoters include but are not limited to metals selected from tin, zinc, copper, gold, silver, and combinations thereof. The preferred metal promoter is tin. Other promoters that can be used are elements selected from Group I and Group II of the Periodic Table, for example.

The catalyst may be supported or unsupported. A supported catalyst is one in which the active catalyst agent is deposited on a support material by a number of methods such as spraying, soaking or physical mixing, followed by drying, calcination and, if necessary, activation through methods such as reduction or oxidation. Materials frequently used as a support may be porous solids with high total surface areas (external and internal) which can provide high concentrations of active sites per unit weight of catalyst. The catalyst support may enhance the function of the catalyst agent. A supported metal catalyst is a supported catalyst in which the catalyst agent is a metal.

A catalyst that is not supported on a catalyst support material is an unsupported catalyst. An unsupported catalyst may be platinum black or a Raney® (W.R. Grace & Co., Columbia, Md.) catalyst, for example. Raney® catalysts have a high surface area due to selectively leaching an alloy containing the active metal(s) and a leachable metal (usually aluminum). Raney® catalysts have high activity due to the higher specific area and allow the use of lower temperatures in hydrogenation reactions. The active metals of Raney® catalysts include at least one of nickel, copper, cobalt, iron, rhodium, ruthenium, rhenium, osmium, iridium, platinum, palladium and compounds thereof.

Promoter metals may also be added to the base Raney® metals to affect selectivity and/or activity of the Raney® catalyst. Promoter metals for Raney® catalysts may be selected from transition metals from Groups IIIA through VIIIA, IB and IIB of the Periodic Table of the Elements. Examples of promoter metals include but are not limited to chromium, molybdenum, platinum, rhodium, ruthenium, osmium, and palladium, typically at about 2% by weight of the total metal, although other weight percentages are possible.

The catalyst support can be any solid, inert substance including, but not limited to, oxides such as silica, alumina and titania; barium sulfate; calcium carbonate; and carbons. The catalyst support can be in the form of powder, granules, pellets or the like.

A preferred support material may be at least one of carbon, alumina, silica, silica-alumina, silica-titania, titania, titania-alumina, barium sulfate, calcium carbonate, strontium carbonate and compounds thereof. Supported metal catalysts can also have supporting materials made from one or more compounds. More preferred supports are carbon, titania and alumina. Further preferred supports are carbons with a surface area greater than about 100 $m^2/g$. A further preferred support is carbon with a surface area greater than about 200 $m^2/g$. Preferably, the carbon has an ash content that is less than about 5% by weight of the catalyst support. The ash content is the inorganic residue (expressed as a percentage of the original weight of the carbon) which remains after incineration of the carbon.

A preferred content of the metal catalyst in the supported catalyst may be from about 0.1% to about 20% of the supported catalyst based on metal catalyst weight plus the support weight. A more preferred metal catalyst content range is from about 1% to about 10% of the supported catalyst.

Combinations of metal catalyst and support system may include any one of the metals referred to herein with any of the supports referred to herein. Preferred combinations of metal catalyst and support include palladium on carbon, palladium on alumina, palladium on titania, platinum on carbon, platinum on alumina, platinum on silica, iridium on silica, iridium on carbon, iridium on alumina, rhodium on carbon, rhodium on silica, rhodium on alumina, nickel on carbon, nickel on alumina, nickel on silica, rhenium on carbon, rhenium on silica, rhenium on alumina, ruthenium on carbon, ruthenium on alumina and ruthenium on silica.

Further preferred combinations of metal catalyst and support include ruthenium on carbon, ruthenium on alumina, palladium on carbon, palladium on alumina, palladium on titania, platinum on carbon, platinum on alumina, rhodium on carbon, and rhodium on alumina.

A more preferred support is carbon. Further preferred supports are those, particularly carbon, that have a BET surface area less than about 2,000 m$^2$/g. Further preferred supports are those, particularly carbon, that have a surface area of about 300 to 1,000 m$^2$/g.

Typically, hydrogenation reactions may be performed at temperatures from about 100° C. to about 300° C. in reactors maintained at pressures from about 1000 to about 3000 psig (7×10~ to about 21×10~Pa gage).

The method of using the catalyst to hydrogenate a SA containing feed can be performed by various known modes of operation. Thus, the overall hydrogenation process can be performed with a fixed bed reactor, various types of agitated slurry reactors, either gas or mechanically agitated, or the like. The hydrogenation process can be operated in either a batch or continuous mode, wherein an aqueous liquid phase containing the precursor to hydrogenate is in contact with a gaseous phase containing hydrogen at elevated pressure and the particulate solid catalyst.

When the catalyst is used to produce BDO and THF at a desired or controlled molar ratio, the hydrogenation is preferably performed at a temperature above about 150° C. and below about 260° C. To obtain a high BDO to THF ratio, the hydrogenation to those desired products should advantageously be performed at or near the lower end of this temperature range. The method and conditions can also advantageously influence the molar ratio during hydrogenation. For example, the liquid phase removal of products from the hydrogenation reactor tends to enhance and maximize BDO production rather than THF. In contrast, continuous vapor removal of product from the hydrogenation reactor tends to maximize THF production at the expense of BDO. Thus, as a practical consideration, low temperature liquid product removal intended to favor BDO production favors the use of fixed bed catalytic reactors. On the other hand, vapor phase product removal intended to favor THF production favors the use of slurry or stirred reactors.

Temperature, solvent, catalyst, reactor configuration, pressure and mixing rate are parameters that can affect the hydrogenation. The relationships among these parameters may be adjusted to effect the desired conversion, reaction rate, and selectivity in the reaction of the process.

A preferred temperature is from about 25° C. to 350° C., more preferably from about 100° C. to about 350° C., and most preferred from about 150° C. to 300° C. The hydrogen pressure is preferably about 0.1 to about 30 MPa, more preferably about 1 to 25 MPa, and most preferably about 1 to 20 MPa.

The reaction may be performed neat, in water or in the presence of an organic solvent. Water is a preferred solvent. Useful organic solvents include but are not limited to hydrocarbons, ethers, alcohols and the like. Alcohols are most preferred, particularly lower alkanols such as methanol, ethanol, propanol, butanol, and pentanol. The reaction should be carried out with selectivity in the range of at least about 70%. Selectivity of at least about 85% is typical. Selectivity is the weight percent of the converted material that is THF, BDO and GBL, where the converted material is the portion of the starting material that participates in the hydrogenation reaction.

The processes may be carried out in batch, sequential batch (i.e. a series of batch reactors) or in continuous mode in equipment customarily employed for continuous processes. The condensate water formed as the product of the reaction is removed by separation methods customarily employed for such separations.

A preferred hydrogenation reactor may be operated under hydrogen pressure and in the presence of structured catalyst chosen from among Ru, Re, Sn, Pb, Ag, Ni, Co, Zn, Cu, Cr, Mn, or mixtures thereof in catalytic amounts. The hydrogen pressure and the temperature of the reactor may be controlled to obtain the desired hydrogenation product. Typically, the reactor feed for hydrogenation is maintained from about 100 C to about 210 C, but more preferably about 135 C to about 150 C.

BDO, THF, and GBL can be separated by known distillation methods. Further, GBL can be partially or fully recycled to the hydrogenation step to maximize the yield of BDO, THF, or both.

EXAMPLES

The processes are illustrated by the following non-limiting representative examples. In a number of the examples, a synthetic, aqueous DAS solution was used in place of an actual clarified DAS-containing fermentation broth. Other examples use an actual clarified DAS-containing fermentation broth.

The use of a synthetic DAS solution is believed to be a good model for the behavior of an actual broth in our processes because of the solubility of the typical fermentation by-products found in actual broth. The major by-products produced during fermentation are ammonium acetate, ammonium lactate and ammonium formate. If these impurities are present during the distillation step, one would not expect them to lose ammonia and form free acids in significant quantities until all of the DAS had been converted to MAS. This is because acetic acid, lactic acid and formic acid are stronger acids than the second acid group of SA (pKa=5.48). In other words, acetate, lactate, formate and even monohydrogen succinate are weaker bases than the dianion succinate. Furthermore, ammonium acetate, ammonium lactate and ammonium formate are significantly more soluble in water than MAS, and each is typically present in the broth at less than 10% of the DAS concentration. In addition, even if the acids (acetic, formic and lactic acids) were formed during the distillation step, they are miscible with water and will not crystallize from water. This means that the MAS reaches saturation and crystallizes from solution (i.e., forming the solid portion), leaving the acid impurities dissolved in the mother liquor (i.e., the liquid portion).

Example 1

This example demonstrates conversion of a portion of DAS into MAS via distillation and recovery of MAS solids from distillation bottoms liquid via cooling-induced crystallization.

A three neck 500 mL round bottom flask was fitted with a thermometer and Dean Stark trap topped with a reflux condenser. The vent from the reflux condenser went to a scrubbing bottle which contained 100 g of a 1.4M acetic acid solution. The flask was charged with 400 g of a 10% DAS aqueous solution (pH 8.5). The contents of the flask were stirred with a magnetic stirrer and heated with a heating mantle to distill off 320.6 g of distillate (an aqueous ammonia solution) which was removed via the Dean Stark trap. Analysis of the distillate indicated that about 20% of the contained ammonia had been removed from the charged DAS during distillation (i.e., the salts in the bottoms liquid were about 40% MAS and about 60% DAS). Only traces of ammonia were found in the scrubbing bottle. The final temperature of the pot as the last drop distilled over was 110° C. The residue (bottoms liquid) in the pot (73.4 g which was about 53% water) was placed in a flask and allowed to cool to room temperature overnight. Upon cooling to room temperature, white needles of MAS were formed. The white solids were separated via vacuum filtration, yielding 14 g of wet crystals (solid portion) and 56 g of mother liquor (liquid portion). A portion of the wet crystals (7 g) was dried overnight in a vacuum oven, yielding 6 g of dried solids which contained 0.4% water as determined by Karl-Fisher analysis. Analysis of the solids portion with HPLC revealed that the solids portion was free of non-MAS nitrogen-containing impurities (e.g., succinimide and succinamide).

Example 2

This example demonstrates mother liquor recycle.

A 1-L round bottom flask was charged with 800 g of a synthetic 4.5% DAS solution, and then a distillation head was attached to the flask. The contents of the flask were distilled at atmospheric pressure leaving 67 g of residue (bottoms liquid) in the flask. The bottoms liquid contained approximately 45% water. Ammonia analyses of the distillates indicate that the first distillation cycle removed about 29% of the ammonia, making a 42/58 mol/mol mixture of DAS and MAS. The residue (bottoms liquid) was then removed from the flask and placed in a beaker equipped with a water bath. The beaker contents were cooled to 20° C. with stirring. Once the residue reached 20° C., it was seeded with a few crystals of MAS and allowed to stir for 30 minutes. The temperature of the bath was then lowered to 15° C. and held for 30 minutes. The temperature was then lowered to 10° C. and held for 30 minutes. The temperature was then cooled to 5° C. and held for 30 minutes and finally to 0° C. where it was held for 30 minutes. The slurry (consisting of solid and liquid portions) was then quickly filtered using a pre-cooled sintered glass filter funnel and vacuum flask. The solids were dried in a vacuum oven yielding 13.9 g of dry MAS solids. The mother liquor (liquid portion, 47.2 g) was then combined with 800 g of synthetic 4.5% DAS solution and distilled, leaving 86.6 g of residue (bottoms liquid). In the second distillation (i.e., mother liquor recycle run) about 28% of the ammonia from the total amount of DAS present was removed. The residue (bottoms liquid) was then cooled (crystallized) in a similar manner. However, the solution became cloudy at 46° C., so it was seeded at 46° C. and allowed to slowly cool to room temperature overnight while stirring. The next day the temperature was slowly ramped down by 5° C. increments to 0° C. The slurry (solid and liquid portions) was filtered as before, and the solids dried, yielding 23.5 g of MAS solids. This is equal to about a 75% recovery of the SA equivalents in the 800 g of fresh DAS solution distilled. The recovered solids from the first cycle were 95% MAS (about 5% water). In the second cycle, the solids were 97% MAS (about 3% water). The mother liquor from the second cycle contained 28.8% SA equivalents (i.e., as SA salts).

Example 3

This example demonstrates the absence of amide and imide species in the solid portion of cooled distillation bottoms.

A 1-L round bottom flask was charged with 800 g of a synthetic 4.5% DAS solution. The flask was fitted with a five tray 1" Oldershaw section which was capped with a distillation head. The distillate was collected in an ice cooled receiver. The contents of the flask were heated with a heating mantel and stirred with a magnetic stirrer. The contents of the flask were distilled giving 721.1 g of an overhead distillate and 72.2 g of a liquid residue in the flask (i.e. distillation bottoms). The aqueous ammonia distillate was titrated revealing a 0.34% ammonia content (i.e., about 55% conversion of DAS to MAS). The hot distillation bottoms (approximately 47% salt solution of DAS and MAS) were then placed in a 125 mL Erlenmeyer flask and allowed to cool slowly to room temperature while stirring over night. The next morning the cloudy solution was cooled to 15° C. and held for 60 minutes, then cooled to 10° C. and held for 60 minutes and finally cooled to 5° C. and held for 60 minutes while stirring. The resulting white slurry was filtered yielding 12.9 g of wet crystals and 55.3 g of mother liquor. The crystals were dissolved in 25.8 g of distilled water. HPLC analysis of the crystal solution revealed no detectable amounts of amide or imide species. However, HPLC analysis of the mother liquor revealed a trace of succinamic acid, but no detectable succinamide or succinimide.

Example 4

This example produces a solid portion of a cooled distillation bottoms that consists essentially of MAS and is substantially free of DAS.

A three neck 1-L round bottom flask was fitted with an addition funnel and a 1" five tray Oldershaw column which was capped with a distillation head. An ice cooled receiver was used to collect the distillate. The flask was charged with 800 g of a synthetic 4.5% DAS solution. The contents of the flask were heated with a heating mantel and stirred with a magnetic stirrer. Distillation was started. While the distillation occurred an additional 1600 g of the 4.5% DAS solution was slowly added to the flask at the same rate as distillate was taken. A total of 2135 g of distillate was taken overhead. Titration of the distillate revealed the overhead was a 0.33% ammonia solution. The hot aqueous distillation bottoms (253.8 g) was removed from the flask and placed in an Erlenmeyer flask. The distillation bottoms were allowed to slowly cool to room temperature while stirring overnight. The contents of the flask were seeded and allowed to stir for 30 minutes. The slurry was then cooled to 15° C. and held for 60 minutes, then 10° C. and held for 60 minutes and finally to 5° C. and held for 60 minutes all while stirring. The slurry was filtered cold and the solids (i.e., the solid portion) washed three times with about 20 g portions of a cold (about 5 C) 20% sodium chloride solution to displace the mother liquor (i.e., the liquid portion). Air was sucked through the cake for several minutes to remove as much liquid as possible. The solids were then dried in a vacuum oven at 75° C. for one hour yielding 7.2 g of white crystals. Carbon and nitrogen analyses of the solids revealed a 4.06 atomic ratio of carbon to nitrogen (i.e., a 1.01 ratio of ammonia to SA or about 99% MAS). That a ratio of 1.00 was not obtained is believed to be attributable to incomplete washing of the solids.

Example 5

This example demonstrates the effect of solvents on ammonia evolution from aqueous DAS. Run 5 is the control experiment where no solvent is present.

The outer necks of a three neck 1-L round bottom flask were fitted with a thermometer and a stopper. The center neck was fitted with a five tray 1" Oldershaw section. The Oldershaw section was topped with a distillation head. An ice cooled 500 mL round bottom flask was used as the receiver for the distillation head. The 1-L round bottom flask was charged with distilled water, the solvent being tested, SA and concentrated ammonium hydroxide solution. The contents were stirred with a magnetic stirrer to dissolve all the solids. After the solids dissolved, the contents were heated with the heating mantle to distill 350 g of distillate. The distillate was collected in the ice cooled 500 mL round bottom flask. The pot temperature was recorded as the last drop of distillate was collected. The pot contents were allowed to cool to room temperature and the weight of the residue and weight of the distillate were recorded. The ammonia content of the distillate was then determined via titration. The results were recorded in Table 1.

TABLE 1

| | Run # | | | | |
|---|---|---|---|---|---|
| | 1 | 2 | 3 | 4 | 5 |
| Name of Acid charged | Succinic | Succinic | Succinic | Succinic | Succinic |
| Wt Acid Charged (g) | 11.81 | 11.79 | 11.8 | 11.79 | 11.8 |
| Moles Acid Charged | 0.1 | 0.1 | 0.1 | 0.1 | 0.1 |
| Wt 28% NH3 Solution Charged (g) | 12.11 | 12.09 | 12.1 | 12.11 | 12.1 |
| Moles NH3 Charged | 0.2 | 0.2 | 0.2 | 0.2 | 0.2 |
| Name of Solvent | Diglyme | PG* | GBL** | butoxy triglycol | none |
| Wt Solvent Charged (g) | 400 | 400.1 | 400 | 400 | 0 |
| Wt Water Charged (g) | 400 | 400 | 400 | 400 | 800 |
| Wt Distillate (g) | 350.5 | 351.6 | 350.1 | 350.7 | 351 |
| Wt Residue (g) | 466.3 | 461.7 | 464.3 | 460.9 | 466 |
| % Mass Accountability | 99.1 | 98.7 | 98.9 | 98.5 | 99.2 |
| Wt % NH3 in distillate (titration) | 0.48 | 0.4 | 0.27 | 0.47 | 0.13 |
| Moles NH3 in distillate | 0.099 | 0.083 | 0.056 | 0.097 | 0.027 |
| % NH3 removed in Distillate | 49.5 | 42 | 28 | 49 | 13.4 |
| % First NH3 removed in Distillate | 99 | 84 | 56 | 98 | 27 |
| % Second NH3 removed in Distillate | 0 | 0 | 0 | 0 | 0 |
| Final Pot Temp (° C.) | 101 | 120 | 110 | 107 | 100 |

*PG is propylene glycol
**GBL is gamma butyrolactone

Example 6

This example produced a solid portion from a cooled distillation bottoms that consists essentially of SA and is substantially free of MAS.

A 300 mL Parr autoclave was charged with 80 g of synthetic MAS and 120 g of water. The autoclave was sealed and the contents stirred and heated to ~200° C. at an autogenic pressure of ~190 psig. Once the contents reached temperature, water was fed to the autoclave at a rate of ~2 g/min and vapor removed from the autoclave at a rate of ~2 g/min with a back pressure regulator. Vapor exiting the autoclave was condensed and collected in a receiver. The autoclave was run under these conditions until a total of 1020 g of water had been fed and a total of 1019 g of distillate collected. The distillate was titrated for ammonia content (0.29% ammonia by weight). This translates into a ~29% conversion of MAS to SA. The contents of the autoclave (194.6 g) were partially cooled and discharged from the reactor. The slurry was allowed to stand under stirring at room temperature over night in an Erlenmeyer flask. The slurry was then filtered and the solids rinsed with 25 g of water. The moist solids were dried in a vacuum oven at 75° C. for 1 hr yielding 9.5 g of SA product. Analysis via an ammonium ion electrode revealed 0.013 mmole ammonium ion/g of solid. HPLC analysis revealed the solids were SA with 0.8% succinamic acid impurity.

Example 7

This example used DAS-containing clarified fermentation broth derived from a fermentation broth containing E. Coli strain ATCC PTA-5132. This example produced a solid portion of a cooled distillation bottoms that consists essentially of MAS and is substantially free of DAS.

A three neck 1-L round bottom flask was fitted with an addition funnel and a 1" five tray Oldershaw column which was capped with a distillation head. An ice cooled receiver was used to collect the distillate. The flask was charged with 800 g of clarified DAS-containing fermentation broth which contained 4.4% DAS, 1% ammonium acetate, 0.05% ammonium formate and 0.03% ammonium lactate. The contents of the flask were heated with a heating mantel and stirred with a magnetic stirrer. Distillation was started. While the distillation ran, an additional 2200 g of the broth solution was slowly added to the flask at the same rate as distillate was removed. A total of 2703 g of distillate was taken as overhead. Titration of the distillate revealed the overhead was a 0.28% ammonia solution. The hot aqueous distillation bottoms solution (269.7 g) was removed from the flask and placed in an Erlenmeyer flask. The distillation bottoms were allowed to slowly cool to room temperature while stirring overnight. The next day, the contents of the flask were seeded and allowed to stir for 30 minutes. The slurry was then cooled to 15° C. and held for 30 minutes, then to 10° C. and held for 30 minutes and finally to 5° C. and held for 30 minutes, all while stirring. The slurry was filtered cold and air was sucked through the cake for several minutes to remove as much liquid as possible. Light brown solids (72.5 g) and dark brown mother liquor (188.4 g with a pH of 6.4) were obtained. The solids were recrystallized to remove the mother liquor by dissolution in 72 g of water at 50° C. The solution was then allowed to slowly cool to room temperature while stirring overnight. The next day the contents of the flask were seeded and stirred for 30 minutes. The slurry was then cooled to 15° C. and held for 30 minutes, then to 10° C. and held for 30 minutes, and finally to 5° C. and held for 30 minutes, all while stirring. The slurry was filtered cold and air was sucked through the cake for several minutes to remove as much liquid as possible, yielding 110 g of brown mother liquor (pH 5.0). The solids were then dried in a vacuum oven at 75° C. for one hour yielding 24 g of off-white crystals. Carbon and nitrogen analyses of the solids revealed a 4.04 molar ratio of carbon to nitrogen (i.e. a 1.01 ratio of ammonia to SA or ~99% MAS). HPLC analysis revealed that the MAS contained 0.07% succinamic acid but no detectable succinimide, succinimide or acetate species. In other words, the MAS was free of DAS and otherwise substantially pure.

Example 8

This example used fermentation derived MAS from a fermentation broth containing E. Coli strain ATCC PTA-5132. This example produced a solid portion from a cooled distillation bottoms that consists essentially of SA and is substantially free of MAS.

A 300 mL Parr autoclave was charged with 80 g of broth derived MAS and 120 g of water. The autoclave was sealed and the contents stirred and heated to ~202° C. at an autogenic pressure of ~205 psig. Once the contents reached temperature, water was fed to the autoclave at a rate of ~2 g/min and vapor was removed from the autoclave at a rate of ~2 g/min with a back pressure regulator. Vapor exiting the autoclave was condensed and collected in a receiver. The autoclave was run under these conditions until a total of 905 g of water had been fed and a total of 908 g of distillate collected. The distillate was titrated for ammonia content (0.38% ammonia by weight). This translates into a ~34% conversion of MAS to SA. The contents of the autoclave (178.2 g) were partially cooled and discharged from the reactor. The slurry was allowed to stand under stirring at room temperature over night in an Erlenmeyer flask. The slurry was then filtered and the solids rinsed with 25 g of water. The moist solids were dried in a vacuum oven at 75° C. for 1 hr yielding 8.5 g of SA product. Analysis via an ammonium ion electrode revealed 0.027 mmole ammonium ion/g of solid. HPLC analysis revealed the solids were SA with 1.4% succinamic acid and 0.1% succinamide impurities.

Example 9

This example used an ammonia releasing solvent to aid deammoniation. This example produced a solid portion from a cooled distillation bottoms that consists essentially of SA and is substantially free of MAS.

A 500 mL round bottom flask was charged with 29 g of MAS solids, 51 g of water and 80 g of triglyme. The flask was fitted with a 5 tray 1" glass Oldershaw column section which was topped with a distillation head. An addition funnel containing 2500 g of water was also connected to the flask. The flask was stirred with a magnetic stirrer and heated with a heating mantel. The distillate was collected in an ice cooled receiver. When the distillate started coming over the water in the addition funnel was added to the flask at the same rate as the distillate was being taken. A total of 2491 g of distillate was taken. The distillate contained 2.3 g of ammonia, as determined by titration. This means ~63% of the MAS was converted to SA. The residue in the flask was then placed in an Erlenmeyer flask and cooled to −5° C. while stirring. After stirring for 30 minutes the slurry was filtered while cold yielding 15.3 g of solids. The solids were dissolved in 15.3 g of hot water and then cooled in an ice bath while stirring. The cold slurry was filtered and the solids dried in a vacuum oven at 100° C. for 2 hrs yielding 6.5 g of succinic acid. HPLC analysis indicated that the solids were SA with 0.18% succinamic acid present.

Example 10

This example used an ammonia releasing solvent to aid deammoniation. This example produced a solid portion of a cooled distillation bottoms that consists essentially of MAS and is substantially free of DAS.

A 500 mL round bottom flask was charged with 80 g of an aqueous 36% DAS solution and 80 g of triglyme. The flask was fitted with a 5 tray 1" glass Oldershaw column section which was topped with a distillation head. An addition funnel containing 700 g of water was also connected to the flask. The flask was stirred with a magnetic stirrer and heated with a heating mantel. The distillate was collected in an ice cooled receiver. When the distillate started coming over the water in the addition funnel was added to the flask at the same rate as the distillate was being taken. A total of 747 g of distillate was taken. The distillate contained 3.7 g of ammonia, as determined by titration. This means ~57% of the ammonia was removed. In other words, all of the DAS was converted into MAS and ~14% of the MAS was further converted into SA. The residue in the flask was then placed in an Erlenmeyer flask and cooled to 5° C. while stirring. After stirring for 30 minutes the slurry was filtered while cold and the solids dried in a vacuum oven at 100° C. for 2 hrs yielding 10.3 g of MAS. Analysis indicated that the solids were MAS with 0.77% succinamic acid and 0.14% succinimide present.

Example 11

This example demonstrates the use of an azeotroping solvent, particularly separation of MAS from other by-products in the broth.

A three neck 500 mL round bottom flask was fitted with a thermometer, a 250 mL addition funnel and a Dean Stark trap topped with a reflux condenser. The flask was charged with 100 g of toluene and 100 g of a ~9% DAS broth solution (which also contained about 1% ammonium acetate and ammonium formate combined). The addition funnel was charged with 250 g of the 9% diammonium succinate broth solution. The contents of the flask were stirred with a magnetic stirrer and heated with a heating mantel bringing the contents to boil. The contents of the addition funnel were added slowly to the flask allowing the toluene-water azeotrope to distill into the Dean-Stark trap with return of the toluene to the flask. After all the contents of the addition funnel had been added (at a rate substantially equal to the distillate) the contents were allowed to further reflux until a total of 277.5 g of aqueous phase had been collected from the Dean Stark trap. The contents of the flask were removed while hot and the two phases separated in a warm separatory funnel. The aqueous phase was cooled in an ice bath while being stirred. The resulting solids were recovered via filtration using a sintered glass funnel. The mother liquor was dark brown and the filtered solids were off-white. The solids were dried in a vacuum oven and analyzed via HPLC. The dried solids (5.7 g) were ~96% monoammonium succinate and ~1% ammonium acetate with the rest being water.

Example 12

A pressure distillation column was constructed using an 8 ft long 1.5" 316 SS Schedule 40 pipe packed with 316 SS Propak packing. The base of the column was equipped with an immersion heater to serve as the reboiler. Nitrogen was injected into the reboiler via a needle valve to pressure. The overhead of the column had a total take-off line which went to a 316 SS shell and tube condenser with a receiver. The receiver was equipped with a pressure gauge and a back pressure regulator. Material was removed from the overhead receiver via blowcasing through a needle valve. Preheated feed was injected into the column at the top of the packing via a pump. Preheated water was also injected into the reboiler via a pump. This column was operated at 30 psig pressure which gave a column temperature of 137° C. The top of the column was fed a synthetic 10% DAS solution at a rate of 5 mL/min and water was fed to the reboiler at a rate of 5 mL/min. The overhead distillate rate was 8 mL/min and the residue rate was 2 mL/min. Titration of the distillate for ammonia indicated that the ~47% of the ammonia had been removed in the distillate (i.e. the conversion to MAS was ~94%). The residue liquid was ~20% MAS and HPLC analysis of the residue indicated an ~3% inefficiency to succinamic acid.

Example 13

A portion of the residue (800 g) from Example 12 was concentrated via a batch distillation to ~59% MAS solution (i.e. 530 g of water was distilled off). The residue was then cooled to 5° C. while stirring. The resulting slurry was filtered and the solids dried in a vacuum oven at 75° C. for 1 hour yielding 52.5 g of MAS solids (i.e. ~32% recovery). HPLC analysis indicated that the solids contained 0.49% succinamic acid and no succinimide.

Example 14

A second portion of the pressure column residue (3200 g) from Example 12 was placed in the evaporative crystallizer and concentrated to ~72% MAS by distilling off 2312 g of water at 60° C. under vacuum. The resulting hot slurry was centrifuged and the recovered solids dried in the vacuum oven at 75° C. for one hour yielding 130.7 g of MAS solids. The mother liquor from the centrifuging step was allowed to cool to room temperature forming a second crop of crystals. This slurry was filtered and the recovered solids were dried at 75° C. under vacuum yielding 114.8 g of MAS solids. Based on the succinate concentration of the feed to the crystallizer, a 20% and 18% recovery was realized for the first and second crops, respectively (i.e. a 38% overall recovery). HPLC analysis of the two crops of solids indicated that the first crop had no detectable succinamic acid and succinimide while the second crop had 0.96% succinamic acid and 0.28% succinimide.

Comparative Example 1

This example demonstrates that an atmospheric distillation of an aqueous MAS solution removes very little ammonia when triglyme is not present.

A 500 mL round bottom flask was charged with 30 g of MAS solids and 120 g of water. The flask was fitted with a 5 tray 1" glass Oldershaw column section which was topped with a distillation head. An addition funnel containing 600 g of water was also connected to the flask. The flask was stirred with a magnetic stirrer and heated with a heating mantel. The distillate was collected in an ice cooled receiver. When the distillate started coming over the water in the addition funnel was added to the flask at the same rate as the distillate was being taken. A total of 606 g of distillate was taken. The distillate contained 0.15 g of ammonia, as determined by titration. This means ~4% of the MAS was converted to SA.

Comparative Example 2

This example demonstrates the decrease in ammonia removal for DAS when triglyme is not present.

A 500 mL round bottom flask was charged with 80 g of an aqueous 36% DAS solution and 80 g of water. The flask was fitted with a 5 tray 1" glass Oldershaw column section which was topped with a distillation head. An addition funnel containing 1200 g of water was also connected to the flask. The flask was stirred with a magnetic stirrer and heated with a heating mantel. The distillate was collected in an ice cooled receiver. When the distillate started coming over the water in the addition funnel was added to the flask at the same rate as the distillate was being taken. A total of 1290 g of distillate was taken. The distillate contained 2.2 g of ammonia, as determined by titration. This means ~44% of the DAS was converted to MAS.

Examples 15-22

A series of batch hydrogenation reactions are performed to evaluate the effectiveness of the catalysts in the hydrogenation of fermentation-derived SA. The reactions are conducted in a stirrable 125 ml autoclave rated up to 2,500 psig.

Hydrogenation experiments conducted by reducing the catalysts in situ for determination of catalyst compositions suitable for hydrogenation of fermentation-derived SA. The experiments are conducted in the 125 ml autoclave as follows: (1) 0.5100 grams of a 1% ruthenium solution derived from $RuCl_3.xH_2O$, 0.2780 g of a $HReO_4$ solution (7.7% Re from $Re_2O_7$), 0.5035 g of particulate acidic carbon (BET 1,500 $m^2/g$), an appropriate amount of 12.5% Sn solution prepared from $SnCl_4; 5H_2O$, and 35 g of 7% aqueous SA solution are mixed in the autoclave; (2) Hydrogen is charged to the reactor to 1,200 psig; (3) The reactor contents are heated to 250° C. at 700 rpm and maintained at 250° C. for 3 hours; (4) The reactor is cooled and vented; and (5) A sample of the slurry in the reactor is filtered and analyzed for BDO, THF, GBL, 1-propanol, and n-butanol using gas chromatography.

Hydrogenation experiments are also conducted by pre-reducing the catalysts deposited on a support to determine catalysts compositions and supports suitable for hydrogenation of fermentation-derived SA. The catalyst is prepared as follows: (1) 2.0305 grams of 1% ruthenium solution derived from $RuCl_3.xH_2O$, 1.104 grams of 7.7% rhenium solution derived from $HReO_4$, appropriate amount of 12.5% Sn solution prepared from $SnCl_4; 5H_2O$, and 2.03 grams of particulate carbon support (average particle size about 20 micron) characterizes as intrinsically acidic (pH=4-4.5) with BET surface area of about 1,500 $m^2/g$ are slurried; (2) The slurry is dried at about 100 to about 120° C., under vacuum and nitrogen purge; (3) The catalysts is reduced under hydrogen-helium flow for about 8 hours at about 300° C.; (4) The catalysts is cooled under helium to about 50° C. and passivated for 30 minutes under 1% $O_2$ in $N_2$. The hydrogenation experiments are conducted in the 125 ml autoclave as follows: (1) About 0.1 to 0.5 g of the catalyst and 35 g of 7% aqueous SA solution are mixed in the autoclave; (2) Hydrogen is charged to the reactor to 1,200 psig; (3) The reactor contents are heated to 250° C. at 700 rpm and maintained at 250° C. for 3 hours; (4) The reactor is cooled and vented; and (5) A sample of the slurry in the reactor is filtered and analyzed for BDO, THF, GBL, 1-propanol, and n-butanol using gas chromatography.

Hydrogenation of SA crystallized from simulated broth composed of reagent grade chemicals and de-ionized water is conducted to determine the effectiveness of the catalysts for SA hydrogenation. SA for hydrogenation is prepared as follows: (1) an aqueous solution consisting of 25% (wt.) SA, 2.5% (wt.) acetic acid, 0.25% (wt.) formic acid, and 0.25% (wt.) lactic acid is prepared at 80° C. in a jacketed kettle equipped with a reflux condenser; (2) The hot solution is cooled to 20° C. by cooling the solution over a 3 hour period following a linear cooling profile; (3) The solution is seeded with 0.1 g of SA crystals at 75° C.; (4) The slurry is allowed to equilibrate at 20° C. for 1 hour; (5) The slurry is filtered with vacuum filtration and washed with 20 g of water; (6) 50 g of the cake (10% wt. moisture) is dissolved in 593 g of deionized water (7% wt. solution).

Hydrogenation of SA crystallized from fermentation-derived broth is conducted to establish the effect of carryover impurities from fermentation. Fermentation-derived SA for hydrogenation is prepared as follows: (1) A fermentation-derived broth containing 4.5% (wt.) DAS, 0.45% (wt.) ammonium acetate, 0.05% (wt.) ammonium formate, and 0.05% (wt.) ammonium lactate is deammoniated and concentrated resulting in a greater than 25% SA solution; (2) The hot solution is cooled to 20° C. by cooling the solution over a 3 hour period following a linear cooling profile; (3) The solution is seeded with 0.1 g of SA crystals at 75° C.; (4) The slurry is allowed to equilibrate at 20° C. for 1 hour; (5) The slurry is filtered with vacuum filtration and washed with 20 g of water; (6) 50 g of the cake (10% wt. moisture) is dissolved in 593 g of deionized water (7% wt. solution).

Representative results are presented in Examples 15-22 in Table 2.

TABLE 2

Representative hydrogenation results

| Ex. | Catalysts | SA | BDO | THF | GBL | PrOH | BuOH |
|---|---|---|---|---|---|---|---|
| 15 | 1% Ru: 4% Re[a] | S | 0.08 | 16.9 | 0.08 | 1.45 | 1.21 |
| 16 | 1% Ru: 4% Re[a] | F | 0.08 | 16.9 | 0.08 | 1.45 | 1.21 |
| 17 | 1% Ru: 0.8% Re: 0.4%[a] | S | | | | | |
| 18 | 1% Ru: 0.8% Re: 0.4%[a] | F | | | | | |
| 19 | 1% Ru: 4% Re[b] | S | 0.88 | 14.8 | 0.29 | 2.16 | 1.59 |
| 20 | 1% Ru: 4% Re[b] | F | 0.88 | 14.8 | 0.29 | 2.16 | 1.59 |
| 21 | 1% Ru: 0.8% Re: 0.4%[b] | S | | | | | |
| 22 | 1% Ru: 0.8% Re: 0.4%[b] | F | | | | | |

S = SA derived from simulated broth derived from reagent chemicals,
F = SA derived from fermentation broth,
[a] = catalyst reduced in situ,
[b] = Pre-reduced catalytst,
PrOH = propanol, and
BuOH = butanol.

Although our processes have been described in connection with specific steps and forms thereof, it will be appreciated that a wide variety of equivalents may be substituted for the specified elements and steps described herein without departing from the spirit and scope of this disclosure as described in the appended claims.

The invention claimed is:

1. A process for making a hydrogenated product comprising:
    (a) providing a clarified fermentation broth containing an ammonium salt of succinic acid;
    (b) distilling the broth to form a first overhead that comprises water and ammonia, and a first liquid bottoms that comprises MAS, at least some DAS, and at least about 20 wt % water;
    (c) cooling and/or evaporating the first bottoms, and optionally adding an antisolvent to the bottoms, to attain a temperature and composition sufficient to cause the first bottoms to separate into a DAS-containing liquid portion and a MAS-containing first solid portion that is substantially free of DAS;
    (d) separating the first solid portion from the first liquid portion;
    (e) recovering the first solid portion;
    (f) dissolving the first solid portion in water to produce an aqueous MAS solution;
    (g) distilling the aqueous MAS solution at a temperature and pressure sufficient to form a second overhead that comprises water and ammonia, and a second bottoms that comprises a major portion of SA, a minor portion of MAS, and water;
    (h) cooling the second bottoms to cause the second bottoms to separate into a second liquid portion and a second solid portion that consists essentially of SA and is substantially free of MAS;
    (i) separating the second solid portion from the second liquid portion;
    (j) recovering the second solid portion;
    (k) hydrogenating the second solid portion in the presence of at least one hydrogenation catalyst to produce the hydrogenated product comprising at least one of THF, GBL or BDO; and
    (l) recovering the hydrogenated product.

2. The process of claim 1, further comprising purifying the second solid portion before step k.

3. The process of claim 2, further comprising dissolving the second solid portion in a solvent to form a solution.

4. The process of claim 1, wherein step k is conducted such that THF is recovered in a vapor phase.

5. The process of claim 1, wherein step k is conducted such that BDO is recovered in a liquid phase.

6. The process of claim 1, wherein the hydrogenation catalyst comprises at least one metal from Group VIII of the Periodic Table of the Elements.

7. The process of claim 6, wherein the at least one metal consists essentially of:
    (i) about 0.5 to about 10% by weight ruthenium, and
    (ii) about 2.0 to about 20% by weight rhenium,
based on total weight of the catalyst.

8. The process of claim 7, further comprising about 0.1 to about 5.0% by weight of tin.

9. The process of claim 1, wherein the catalyst is supported on at least one selected from the group consisting of carbon, silica, alumina, silica-alumina, silica-titania, titania, titania-alumina, barium sulfate, calcium carbonate and strontium carbonate.

10. The process of claim 1 wherein the ammonium salt of succinic acid is selected from the group consisting of DAS and MAS.

* * * * *

UNITED STATES PATENT AND TRADEMARK OFFICE
CERTIFICATE OF CORRECTION

PATENT NO. : 8,193,375 B2  
APPLICATION NO. : 13/213565  
DATED : June 5, 2012  
INVENTOR(S) : Fruchey et al.

Page 1 of 1

It is certified that error appears in the above-identified patent and that said Letters Patent is hereby corrected as shown below:

On the Title Page

Item (73) Assignee, please change "S.ä.r.l." to --S.á.r.l.--.

Signed and Sealed this
Thirtieth Day of October, 2012

David J. Kappos
*Director of the United States Patent and Trademark Office*

UNITED STATES PATENT AND TRADEMARK OFFICE
CERTIFICATE OF CORRECTION

PATENT NO. : 8,193,375 B2
APPLICATION NO. : 13/213565
DATED : June 5, 2012
INVENTOR(S) : Fruchey et al.

Page 1 of 1

It is certified that error appears in the above-identified patent and that said Letters Patent is hereby corrected as shown below:

On the Title Page

Item (73) Assignee, please change "S.ä.r.l." to --S.á.r.l.--.

This certificate supersedes the Certificate of Correction issued October 30, 2012.

Signed and Sealed this
First Day of January, 2013

David J. Kappos
*Director of the United States Patent and Trademark Office*

UNITED STATES PATENT AND TRADEMARK OFFICE
CERTIFICATE OF CORRECTION

PATENT NO. : 8,193,375 B2  
APPLICATION NO. : 13/213565  
DATED : June 5, 2012  
INVENTOR(S) : Fruchey et al.

Page 1 of 1

It is certified that error appears in the above-identified patent and that said Letters Patent is hereby corrected as shown below:

On the Title Page

Item (73) Assignee, please change "S.ä.r.l." to --S.à.r.l.--.

This certificate supersedes the Certificates of Correction issued October 30, 2012 and January 1, 2013.

Signed and Sealed this  
Fifteenth Day of October, 2013

Teresa Stanek Rea  
*Deputy Director of the United States Patent and Trademark Office*